(12) United States Patent
Tsai et al.

(10) Patent No.: US 10,008,678 B2
(45) Date of Patent: *Jun. 26, 2018

(54) ORGANIC ELECTROLUMINESCENT MATERIALS AND DEVICES

(71) Applicant: Universal Display Corporation, Ewing, NJ (US)

(72) Inventors: Jui-Yi Tsai, Lawrenceville, NJ (US); Walter Yeager, Yardley, PA (US); Jason Brooks, Philadelphia, PA (US); Scott Beers, Flemington, NJ (US); Gregory S. Kottas, Yardley, PA (US); Edward Barron, Hamilton, NJ (US); Raymond Kwong, Plainsboro, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 923 days.

This patent is subject to a terminal disclaimer.

(21) Appl. No.: 14/330,351

(22) Filed: Jul. 14, 2014

(65) Prior Publication Data

US 2014/0319504 A1 Oct. 30, 2014

Related U.S. Application Data

(63) Continuation of application No. 12/632,251, filed on Dec. 7, 2009, now Pat. No. 8,815,415.

(Continued)

(51) Int. Cl.
*H01L 51/54* (2006.01)
*C09K 11/06* (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
None
See application file for complete search history.

(56) References Cited

U.S. PATENT DOCUMENTS 4,769,292 A 9/1988 Tang et al.
5,061,569 A 10/1991 VanSlyke et al.
(Continued)

FOREIGN PATENT DOCUMENTS

EP 0650955 5/1995
EP 1725079 11/2006
(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Marie R. Yamnitzky
(74) *Attorney, Agent, or Firm* — Duane Morris LLP

(57) ABSTRACT

Imidazo[1,2-f]phenanthridine compounds are provided. The compounds have a twisted aryl moiety further substituted by alkyl having four or more atoms. The compounds may be used in organic light emitting devices, particularly as emissive dopants, providing devices with improved efficiency, stability, and manufacturing. In particular, the compounds provided herein may be used in blue devices having high efficiency.

17 Claims, 3 Drawing Sheets

Related U.S. Application Data

(60) Provisional application No. 61/122,259, filed on Dec. 12, 2008.

(51) Int. Cl.
  *H01L 51/00* (2006.01)
  *C07F 15/00* (2006.01)
  *H05B 33/14* (2006.01)
  *H01L 51/50* (2006.01)

(52) U.S. Cl.
  CPC ...... *H05B 33/14* (2013.01); *C09K 2211/1044* (2013.01); *C09K 2211/1048* (2013.01); *C09K 2211/1051* (2013.01); *C09K 2211/185* (2013.01); *H01L 51/0072* (2013.01); *H01L 51/0074* (2013.01); *H01L 51/5016* (2013.01)

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,333,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 7,915,415 B2 * | 3/2011 | Knowles et al. ... C07F 15/0033 313/504 |
| 8,815,415 B2 * | 8/2014 | Tsai et al. ......... C07F 15/0033 257/E51.044 |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0068526 A1 | 4/2003 | Kamatani et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0272692 A1 | 11/2008 | Hashimoto et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0066226 A1 * | 3/2009 | Sugita et al. ........ C07D 405/14 313/504 |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | |
|---|---|---|
| EP | 2034538 | 3/2009 |
| JP | 200511610 | 1/2005 |
| JP | 2005097549 | 4/2005 |
| JP | 2007123392 | 5/2007 |
| JP | 2007254297 | 10/2007 |
| JP | 2008074939 | 4/2008 |
| JP | 2010062023 | 3/2010 |
| WO | 2001039234 | 5/2001 |
| WO | 2002002714 | 1/2002 |
| WO | 02015645 | 2/2002 |
| WO | 02/44189 | 6/2002 |
| WO | 2003040257 | 5/2003 |
| WO | 2003060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002623 | 1/2007 |
| WO | 2007004380 | 1/2007 |
| WO | 2007063754 | 6/2007 |
| WO | 2007063796 | 6/2007 |
| WO | 2007095118 | 8/2007 |
| WO | 2008056746 | 5/2008 |
| WO | 2008101842 | 8/2008 |
| WO | 2008132085 | 11/2008 |
| WO | 2008140114 | 11/2008 |
| WO | 2008142976 | 11/2008 |
| WO | 2008143059 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |

(56) References Cited

FOREIGN PATENT DOCUMENTS

| WO | 2009066779 | 5/2009 |
|---|---|---|
| WO | 2009086028 | 7/2009 |
| WO | 2009100991 | 8/2009 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90:183503-1-183503-3, (2007).
Baldo et al., Highly Efficient Phosphorescent Emission from Organic Electroluminescent Devices. Nature, vol. 395, 151-154, (1998).
Baldo et al., Very high-efficiency green organic light-emitting devices based on electrophosphorescence, Appl. Phys. Lett., vol. 75, No. 1, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1:15-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Snythetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C, et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shin-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis (dimesitylboryl)-2.2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metal, 91:209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic LIght-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).

(56) References Cited

OTHER PUBLICATIONS

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

ORGANIC ELECTROLUMINESCENT MATERIALS AND DEVICES

This application is a continuation of U.S. application Ser. No. 12/632,251, filed Dec. 7, 2009, now U.S. Pat. No. 8,815,415, which claims priority to U.S. Provisional Application No. 61/122,259, filed Dec. 12, 2008, the disclosures of which are expressly incorporated herein by reference in their entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and specifically phosphorescent organic materials used in such devices. More specifically, the invention relates to imidazo[1,2-f]phenanthridine compounds and devices containing these compounds.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) indium, denoted Ir(ppy)$_3$, which has the structure of Formula I:

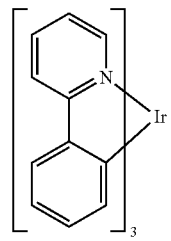

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than"

or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Compounds are provided having the formula:

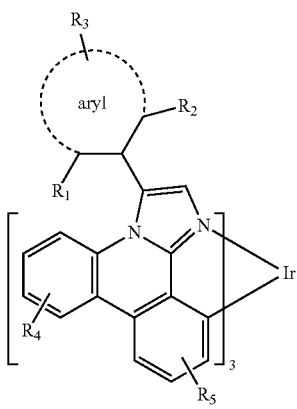

FORMULA I $R_1$ and $R_2$ are independently selected from the group consisting of hydrogen, alkyl, and aryl. At least one of $R_1$ and $R_2$ is an alkyl having four or more atoms. $R_3$, $R_4$, and $R_5$ may represent mono, di, tri, or tetra substitutions. $R_3$, $R_4$, and $R_5$ are independently selected from the group consisting of hydrogen, alkyl, and aryl. In one aspect, $R_1$ and $R_2$ are the same. In another aspect, $R_1$ and $R_2$ are different. In yet another aspect, one of $R_1$ and $R_2$ is an aryl.

The alkyl having four or more atoms may be a branched alkyl, a cyclic alkyl, a bicyclic alkyl, or a multicyclic alkyl.

In one aspect, the alkyl having four or more atoms may contain all carbon atoms. In another aspect, the alkyl having four or more atoms may be a substituted alkyl which may further contain at least one of oxygen atoms, nitrogen atoms, and sulfur atoms.

The compound may have the formula

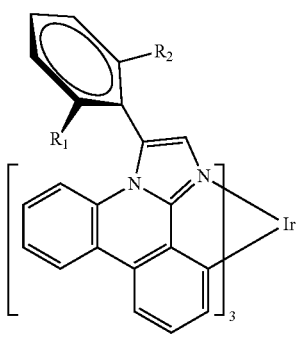

Specific examples of the compound are provided including Compounds 1-36. Preferably, the compound is Compound 1 or Compound 2.

Additionally, a compound including a ligand is provided. The ligand has the formula:

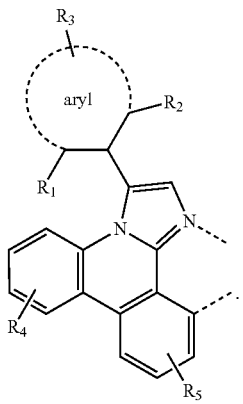

$R_1$ and $R_2$ are independently selected from the group consisting of hydrogen, alkyl, and aryl, and at least one of $R_1$ and $R_2$ is an alkyl having four or more atoms. $R_3$, $R_4$, and $R_5$ may represent mono, di, tri, or tetra substitutions. $R_3$, $R_4$, and $R_5$ are independently selected from the group consisting of hydrogen, alkyl, and aryl.

An organic light emitting device is also provided. The device has an anode, a cathode, and an organic layer disposed between the anode and the cathode. The organic layer further comprises a compound having FORMULA I. Preferably the organic layer is an emissive layer having a host and an emissive dopant, and the compound is the emissive dopant.

A consumer product is also provided. The product contains a device that has an anode, a cathode, and an organic layer disposed between the anode and the cathode, wherein the organic layer further comprises a compound having FORMULA I.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
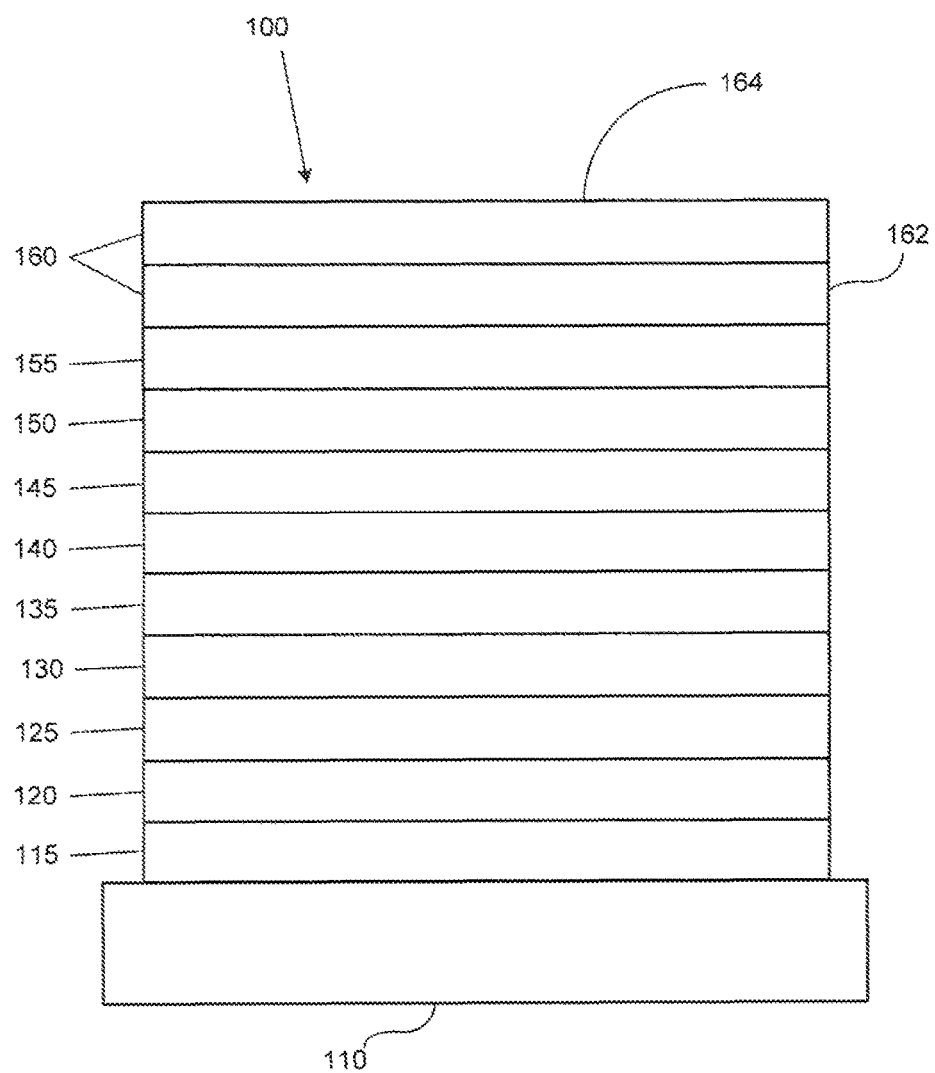
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
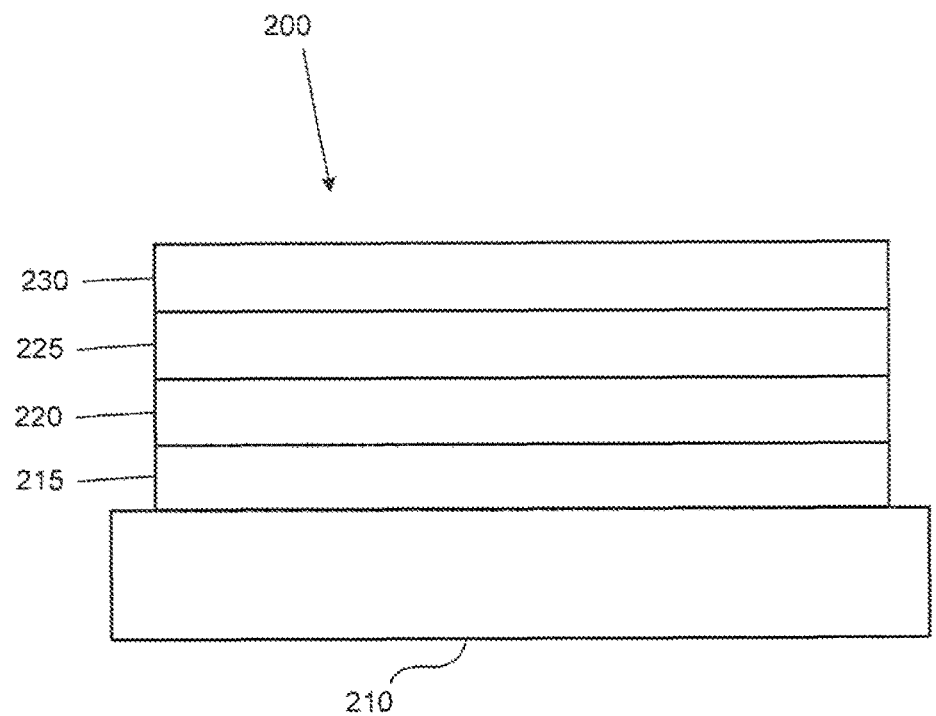
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 maybe referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
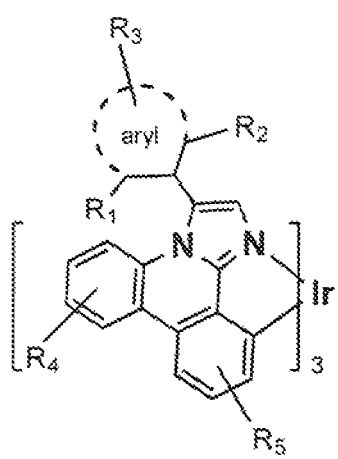
FIG. 3 shows an imidazo[1,2-f]phenanthridine compound.

Imidazo 1,2-f]phenanthridine (herein called "imidazophenanthridine") compounds containing a twisted aryl moiety further substituted with an alkyl having four or more atoms are provided. FIG. 3 shows a structure for such substituted imidazophenanthridine compounds. These compounds can be used in phosphorescent organic light emitting devices to provide high efficiency, high stability, long lifetime, improved manufacturing and improved color. Specifically, phosphorescent organic light emitting devices containing imidazo[1,2-f]phenanthridine iridium complexes containing a twisted aryl moiety further substituted with bulky alkyl groups (i.e., alkyl groups containing four or more atoms) as the emitting materials can have significantly higher efficiency than devices containing emitting materials which lack the bulky alkyl substituted twisted aryl group. The compounds may be used as phosphorescent emissive dopants in color OLEDs and white OLEDs. In particular, the compounds can be used as emissive dopants in high efficiency blue phosphorescent OLEDs. The development of dopant materials, such as the substituted imidazophenanthridine compounds provided herein, suitable for use in blue emissive devices are particularly desirable.

The indium imidazo[1,2-f]phenanthridine complexes contain a twisted aryl moiety that is further substituted at the 2 and/or n position, wherein n is the number of atoms in the aryl moiety, and the atom of the aryl moiety connected to the imiadzole is the 1 position, with an alkyl group having four or more atoms. These compounds containing bulky alkyl groups may have high photoluminescence (PL) and high electroluminescence (EL) efficiencies. Without being bound by theory, it is believed that the bulky alkyl substituents on the twisted aryl provide steric protection of the imidazole which is especially sensitive to self-quenching interactions. Imidazoles are prone to stacking because of their more polar nature, and the stacking of the imidazole rings may readily deactivates the active state of the complex via self-quenching. It is thought that bulky alkyl substituents present on the twisted aryl moiety of the compound may prevent stacking of the imidazole rings thereby inhibiting self-quenching. In particular, the three dimensional arrangement of the 2, n alkyl groups having four or more atoms is particularly good at protecting the imidazole heterocycle. In addition, the steric protection provided by the 2, n bulky alkyl substituents may then result in an increased quantum yield. Therefore, the addition of bulky alkyl groups to the aryl may improve device efficiency and device lifetime.

While substituted imidazophenanthridine compounds and their use in OLEDs are known, several problems may be associated with devices containing these compounds. For example, as shown in Table 2, substitution with an alkyl group at the 2 position of imidazophenanthridine, such as in Comparative Example 1, high PL and EL efficiencies can be obtained but the device lifetime is poor. Another example is the twisted aryl at the 3 position of imidazophenanthridine with less bulky $R_1$ and $R_2$ groups (e.g., alkyl containing one, two, or three atoms), such as in Comparative Example 2, can increase the device lifetime, but PL efficiency is low, thus resulting in low device efficiency. Therefore, it is desirable to develop a dopant that can provide high device efficiency and high device lifetime.

In order to increase efficiency and maintain lifetime, compounds were synthesized in which bulky alkyl groups were added to the 2 and/or n positions of the twisted aryl moiety of the imidazophenanthridine compound. Both the size of the alkyl group (i.e., a bulky alkyl having four or more atoms) and the site of substitution (i.e., the 2 and/or n positions of the twisted aryl moiety) are believed to be important for the beneficial properties of the compounds provided herein. As discussed above, the bulky alkyl groups can improve the quantum yield and provide high efficiency likely due to steric protection of the imidazole. The bulky alkyl substituents may also lead to improved luminescence quantum yield by protecting the imidazole from reacting with oxygen, a pathway which decreases quantum yield. Again, the position of the bulky alkyl is thought to be important in order to obtain increased quantum yield. For example, a compound containing a bulky alkyl substituent at another position on the imidazophenanthridine compound may not demonstrate the same EL and PL (see Comparative example 3 in Table 2). Moreover, the compounds provided herein may provide devices having long lifetimes. For example, device lifetimes for inventive compound, such as Compounds 1 and 2, can be significantly longer then device lifetimes for other imidazophenanthridine compounds lacking the bulky alkyl substituted twisted aryl (see Table 2). In addition, certain bulky alkyl groups at the 2 and n positions may provide cleaner sublimation thus improving device performance and processing.

Asymmetric compounds in which $R_1$ and $R_2$ are not the same, but at least one of $R_1$ and $R_2$ is an alkyl having four or more atoms, are also provided. These asymmetrical compounds may provide improved lifetime and efficiency as well as offer several additional advantages. For example, asymmetric compounds may offer advantages for sublimation and processing. Asymmetric compounds maintain the advantages of the symmetric compounds discussed above, and may further benefit from having a less bulky (e.g., hydrogen, alkyl having 3 or fewer atoms) substituent at the other of $R_1$ and $R_2$. By having one less bulky substituent and one more bulky substituent, these compounds may have a lower molecular weight and thus may be expected to have a lower sublimation temperature while preserving the benefits of high luminescence quantum yield. So then, asymmetric compounds may provide a means to further tune the properties of the emissive dopant having beneficial properties in device lifetime and device stability.

In addition, synthesis of the imidazophenanthridine compounds containing a twisted aryl further substituted by alkyl having four or more atoms provided herein involves only one intermediate. Therefore, the synthesis of these compounds may be advantageous compared to the synthesis of other compounds which require more steps and more intermediates in order to yield product.

Imidazo[1,2-f]phenanthridine compounds are provided, which may be advantageously used in OLEDs, having the formula:

FORMULA I

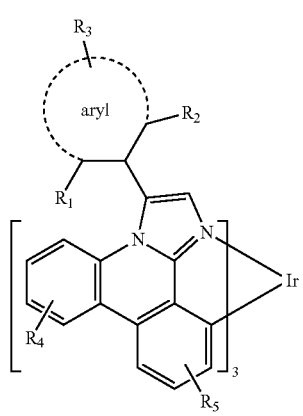

where $R_1$ and $R_2$ are independently selected from the group consisting of hydrogen, alkyl, and aryl, and at least one of $R_1$ and $R_2$ is an alkyl having four or more atoms. $R_3$, $R_4$, and $R_5$ may represent mono, di, tri, or tetra substitutions, and $R_3$, $R_4$, and $R_5$ are independently selected from the group consisting of hydrogen, alkyl, and aryl. In one aspect, $R_1$ and $R_2$ are the same. In another aspect, $R_1$ and $R_2$ are different. In yet another aspect, one of $R_1$ and $R_2$ is an aryl.

In one aspect, the alkyl having four or more atoms is a branched alkyl. A branched alkyl substituent having four or more atoms may further prevent stacking of the imidazole rings by providing additional bulk (i.e., more atoms) thereby increasing the steric protection provided by the bulky alkyl substituent and improving quantum yield. In another aspect, the alkyl having four or more atoms is a cyclic alkyl. In particular, the cyclic alkyl can be a bicyclic alkyl and a multicyclic alkyl. Similarly, the presence of a cyclic, bicyclic and/or multicyclic alkyl at $R_1$ and $R_2$ may provide increased bulk and greater steric protection thereby improving quantum yield.

In one aspect, the alkyl having four or more atoms contains only carbon atoms. In another aspect, the alkyl having four or more atoms is a heteroalkyl. As used herein, "heteroalkyl" refers to an alkyl having four or more atoms wherein at least one of the atoms is a commonly used heteroatom. As used herein, "heteroatom" refers to an atom other than carbon or hydrogen including, but not limited to, oxygen, nitrogen, phosphorous, sulfur, selenium, arsenic, chlorine, bromine, silicon, and fluoride. Preferably, the heteroalkyl contains an oxygen atom. The heteroalkyl substituent acts as an electron withdrawing group thereby reducing the LUMO level (i.e., increasing electron stability) and improving the device stability. Moreover, based on standard calculations, the heteroalkyl may result in minimal red-shifting of the compound. Thus, these compounds provide good blue emission as well as improved stability, lifetime and processing.

In one aspect, the compound has the formula:

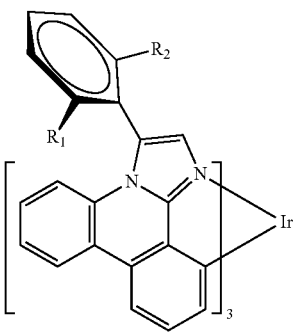

Particular examples of compounds described herein include compounds selected from the group consisting of:

Compound 1

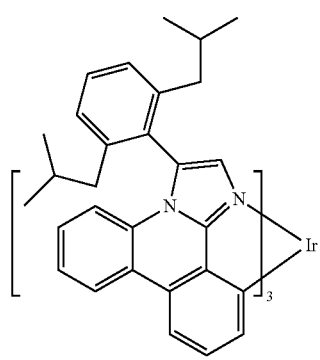

Compound 2

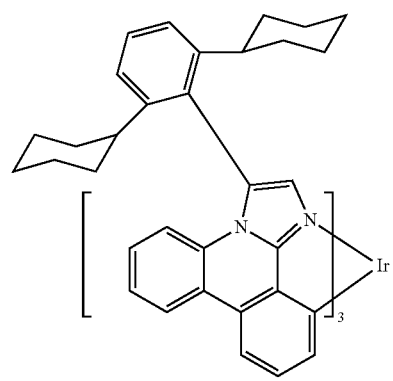

Compound 3

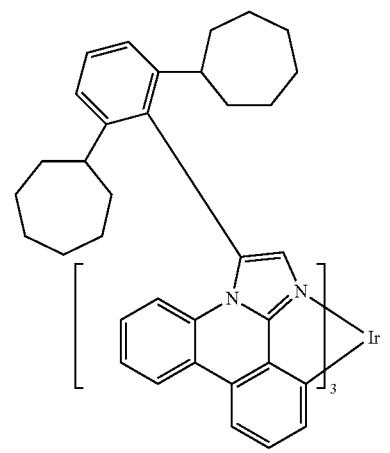

Compound 4
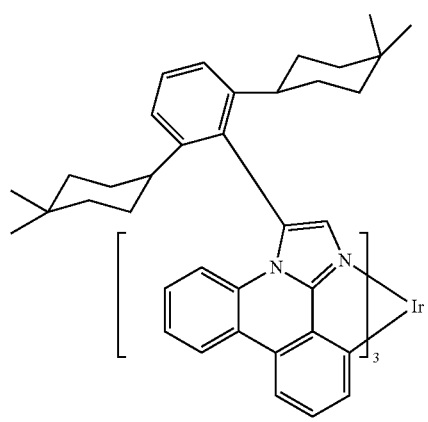
Compound 5
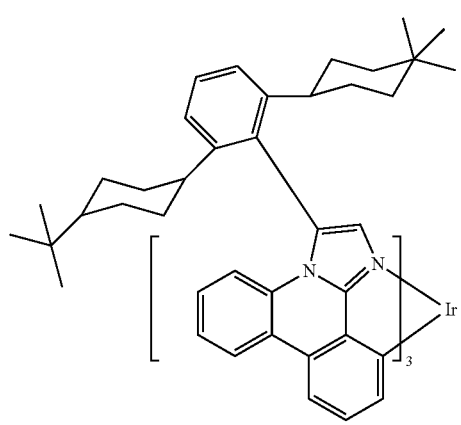
Compound 6
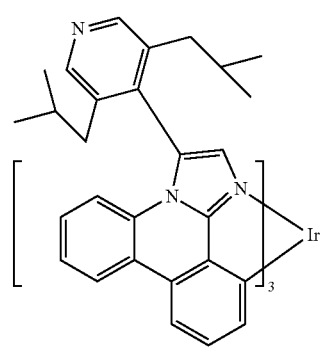
Compound 7
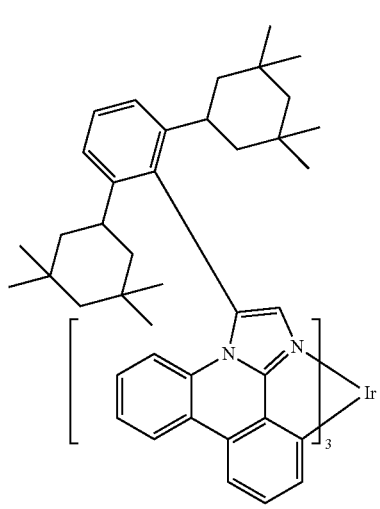
Compound 8
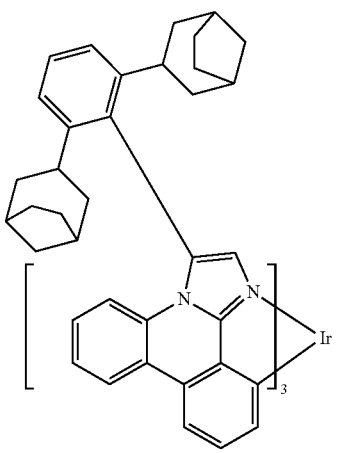
Compound 9
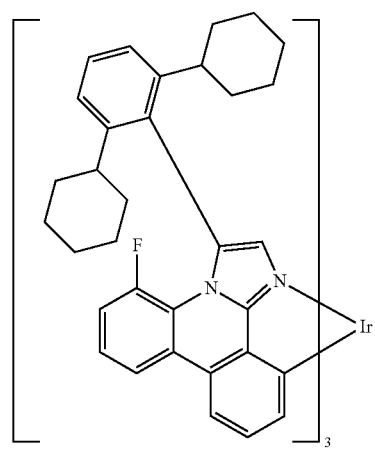

Compound 10
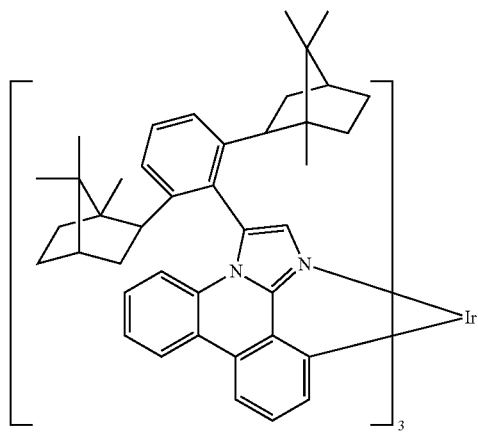
Compound 11
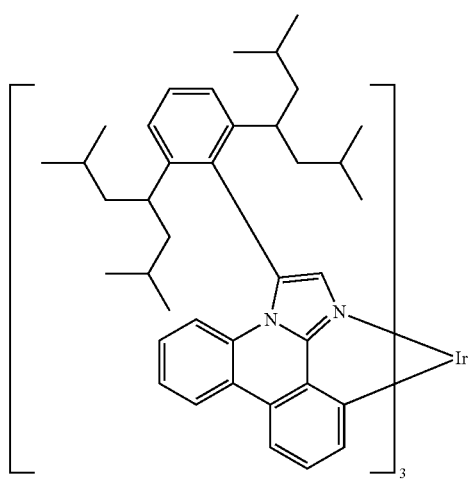
Compound 12
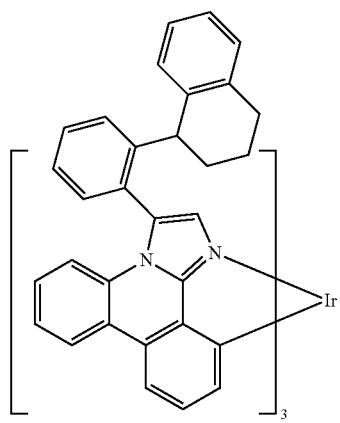
Compound 13
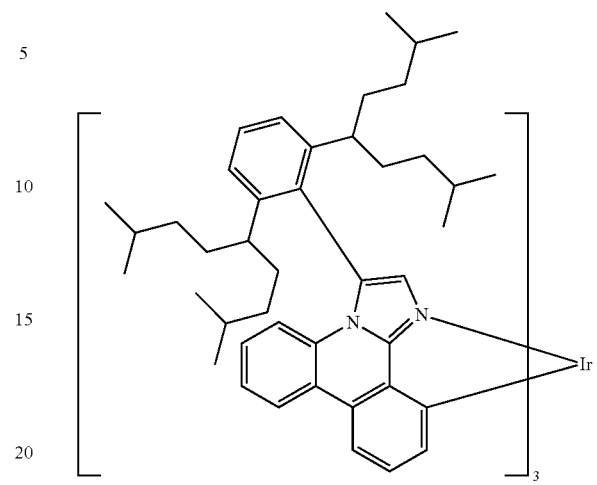
Compound 14
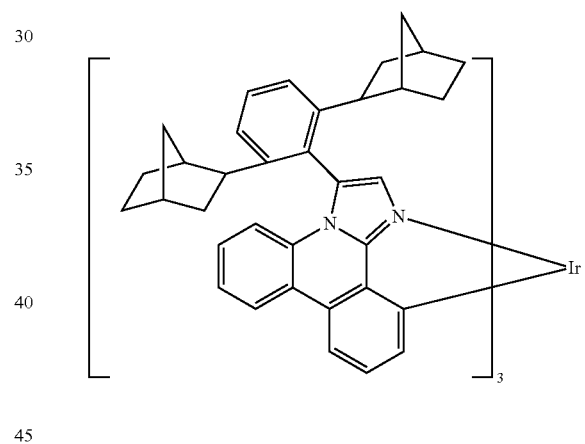
Compound 15
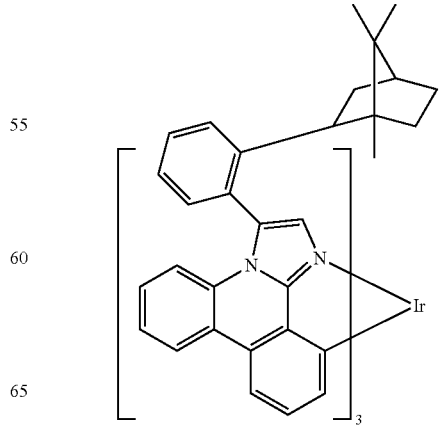

Compound 16
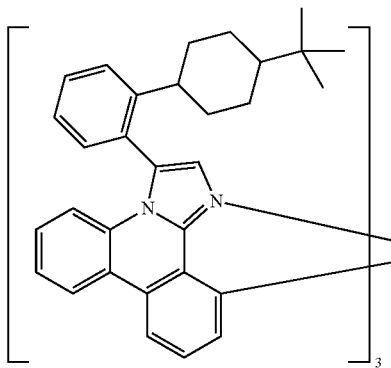
Compound 17
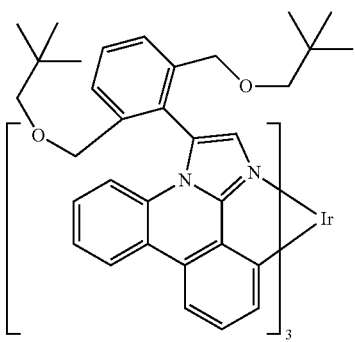
Compound 18
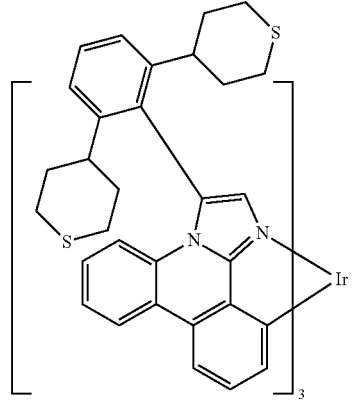
Compound 19
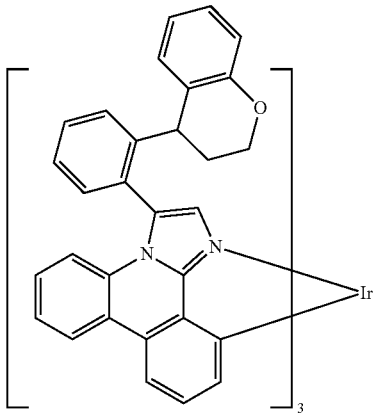
Compound 20
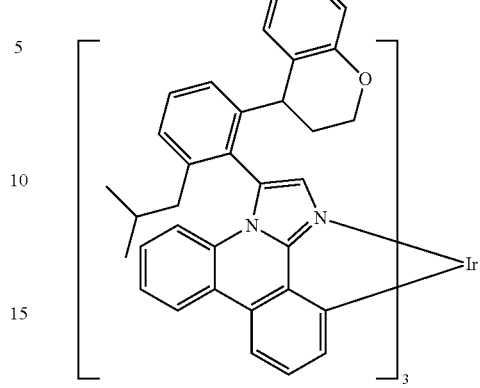
Compound 21
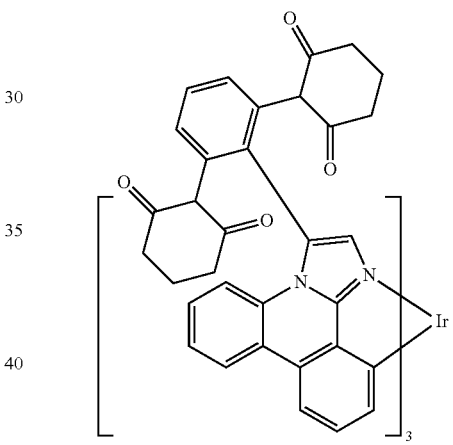
Compound 22
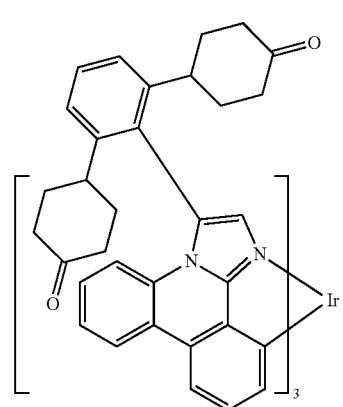

Compound 23
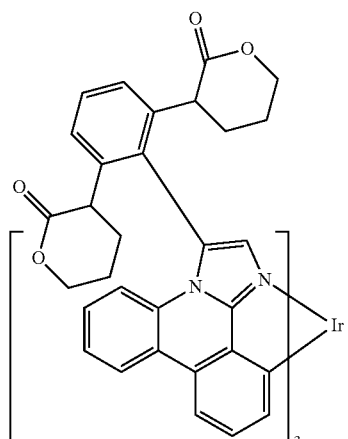
Compound 24
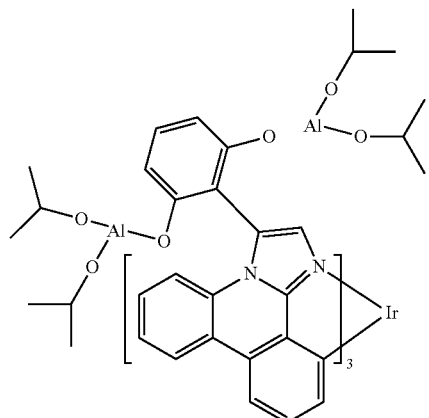
Compound 25
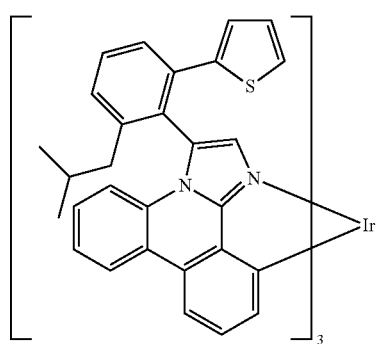
Compound 26
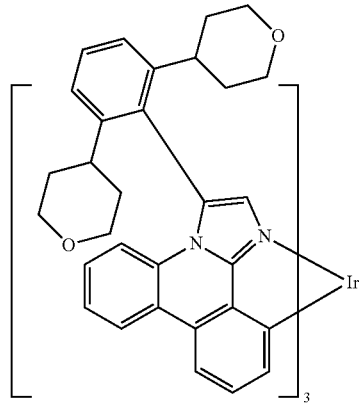
Compound 27
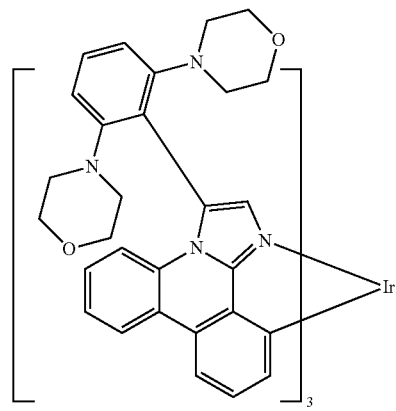
Compound 28
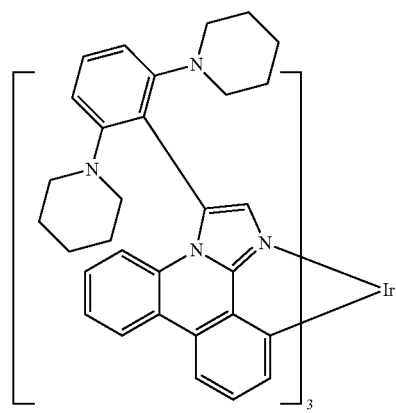

Compound 29
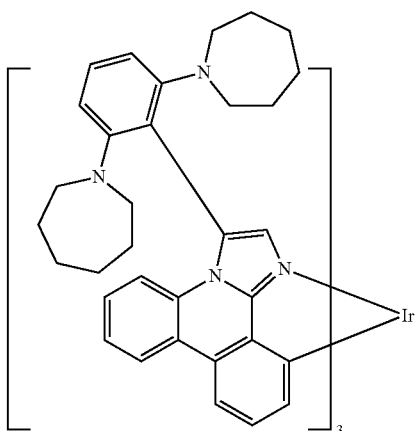
Compound 30
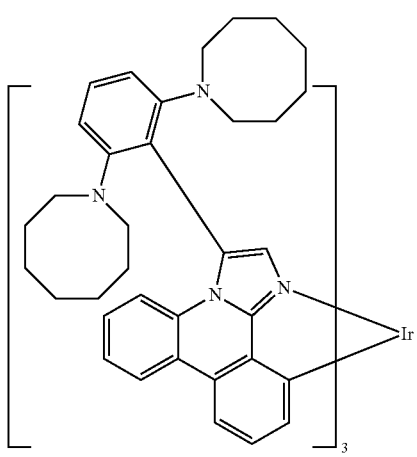
Compound 31
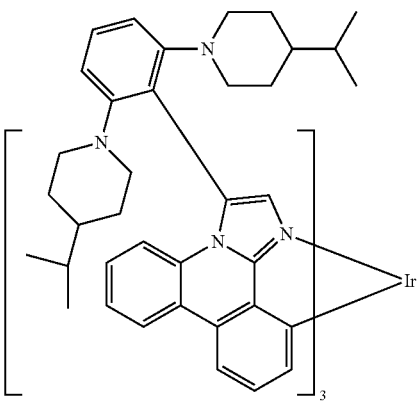
Compound 32
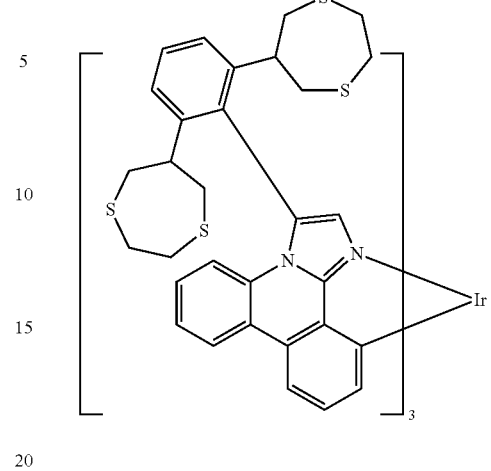
Compound 33
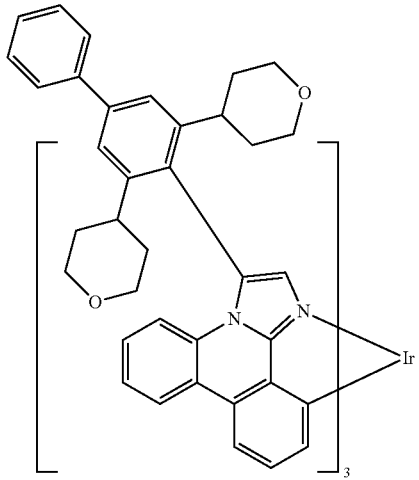
Compound 34
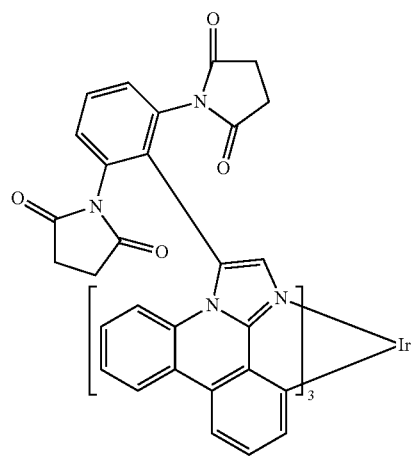

Compound 35

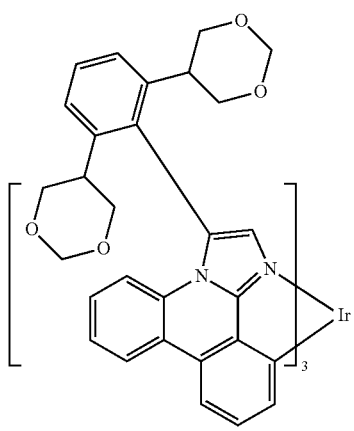

Compound 36

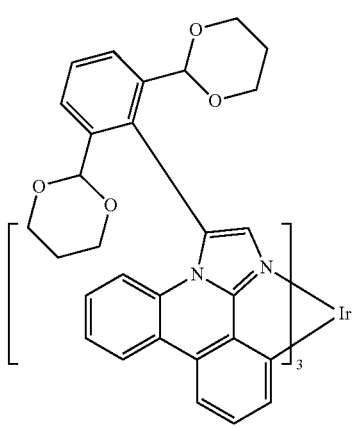

More preferably, the compound is selected from the group consisting of Compound 1 and Compound 2.

A compound including a ligand is also provided, wherein the ligand has the formula:

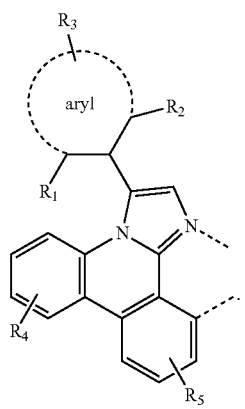

$R_1$ and $R_2$ are independently selected from the group consisting of hydrogen, alkyl, and aryl, and at least one of $R_1$ and $R_2$ is an alkyl having four or more atoms. $R_3$, $R_4$, and $R_5$ may represent mono, di, tri, or tetra substitutions. $R_3$, $R_4$, and $R_5$ are independently selected from the group consisting of hydrogen, alkyl, and aryl. The dashed lines represent attachment of the ligand to a metal. Metals consisting of the non-radioactive metals with atomic numbers greater than 40 may be suitable for use in the complex. For example, the complex may include a metal selected from the group consisting of Re, Ru, Os, Rh, Ir, Pd, Pt, Cu and Au. Preferably, the metal is Ir. Moreover, the complex including the ligand provided may be a homoleptic complex or a heteroleptic complex. Preferably, the complex containing the ligand provided is a tris Ir complex.

Additionally, an organic light emitting device is also provided. The device may include an anode, a cathode, and an organic emissive layer disposed between the anode and the cathode. The organic emissive layer further comprises a compound having FORMULA I. Preferably, the organic layer further comprises a compound selected from the group consisting of:

Compound 1

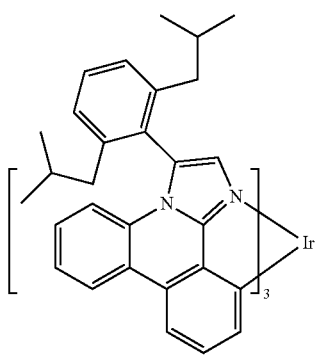

Compound 2

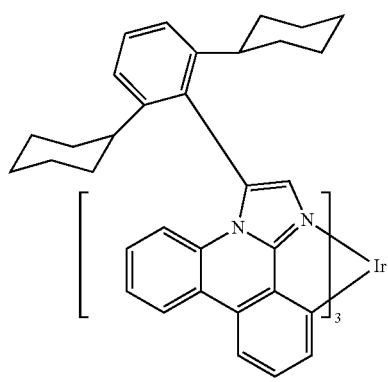

Compound 3

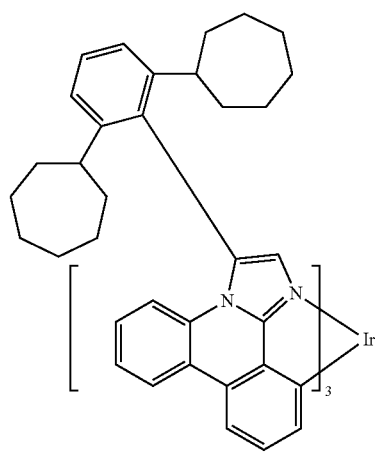

Compound 4
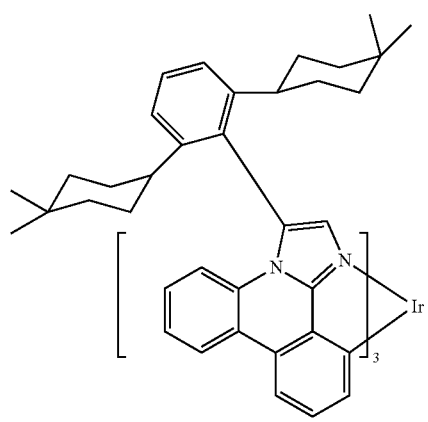
Compound 5
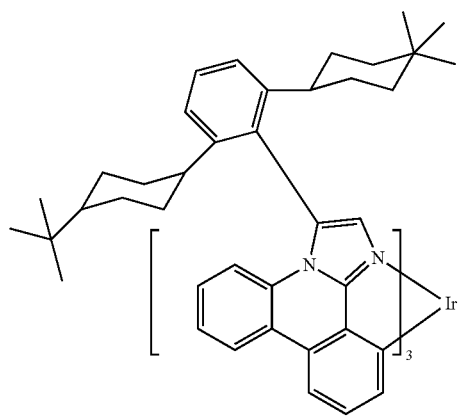
Compound 6
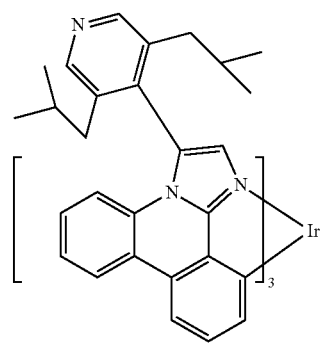
Compound 7
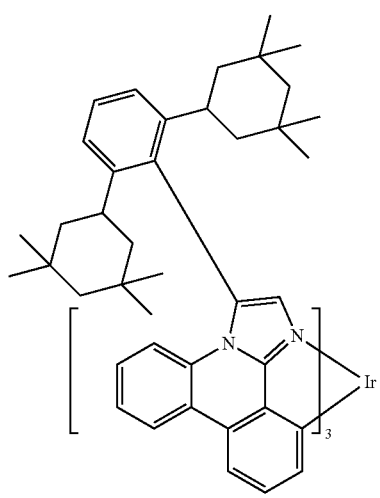
Compound 8
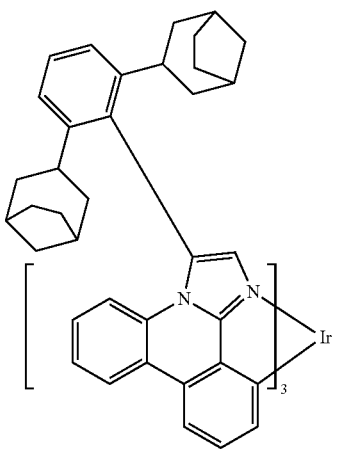
Compound 9
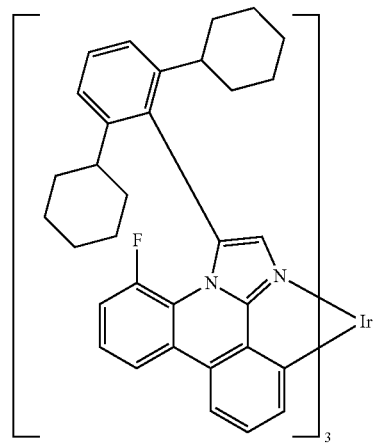

Compound 10
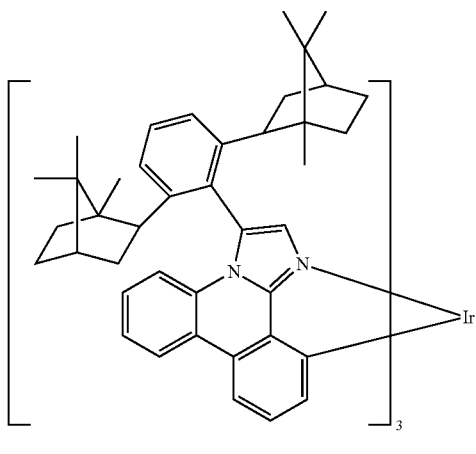
Compound 11
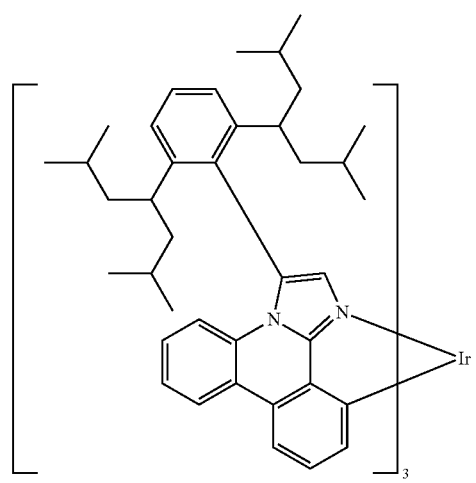
Compound 12
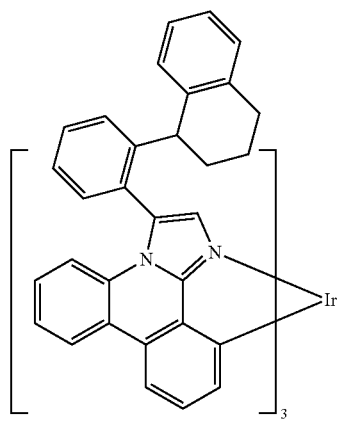
Compound 13
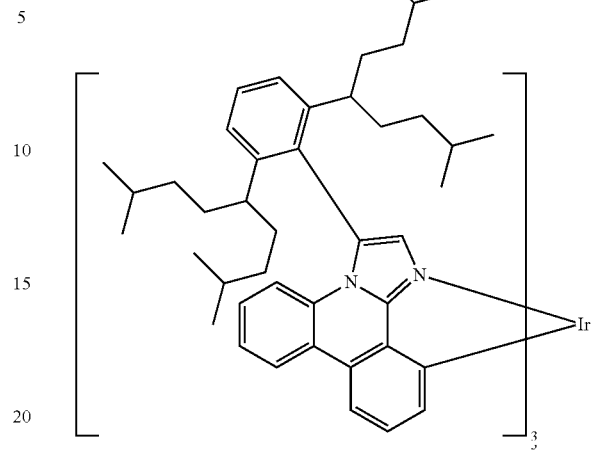
Compound 14
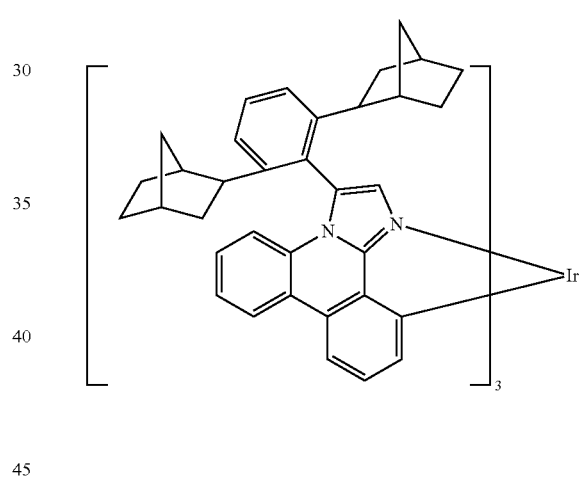
Compound 15
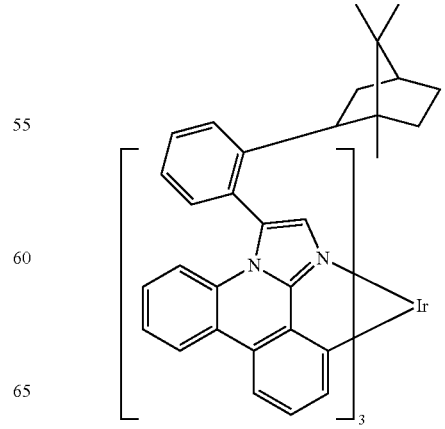

-continued
Compound 16
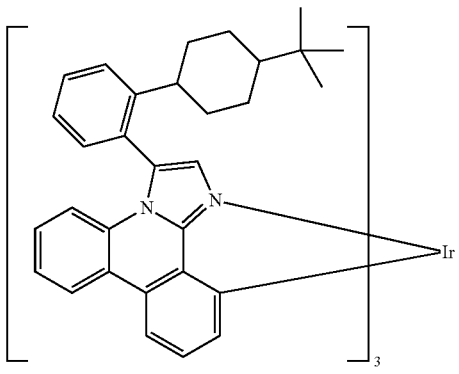
Compound 17
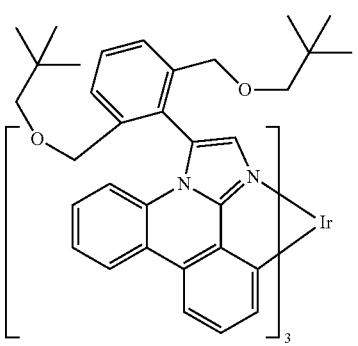
Compound 18
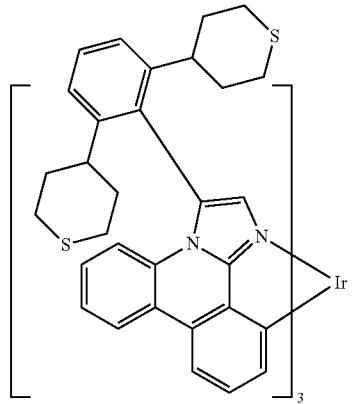
Compound 19
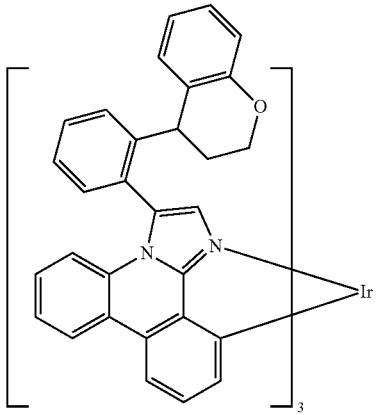
-continued
Compound 20
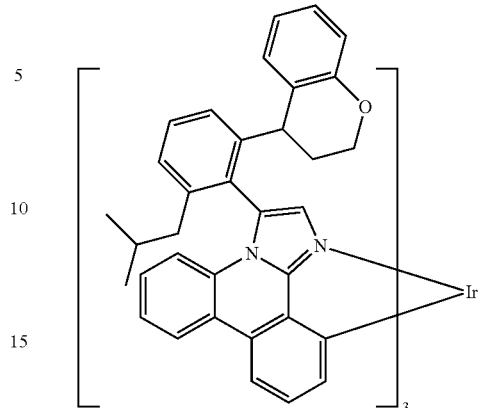
Compound 21
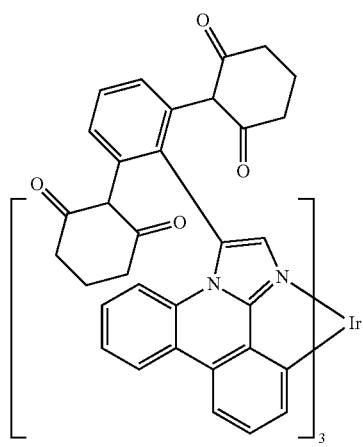
Compound 22
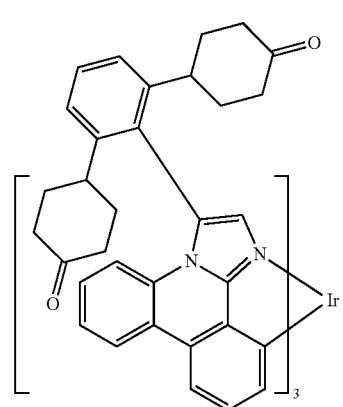

Compound 23
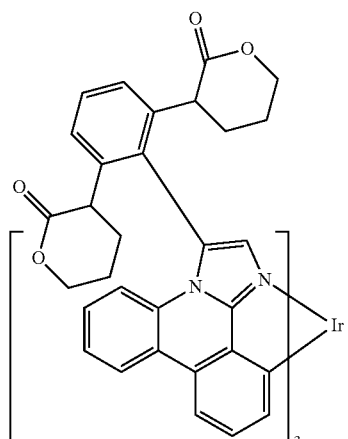
Compound 24
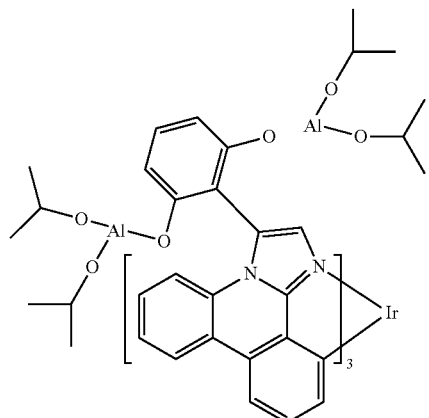
Compound 25
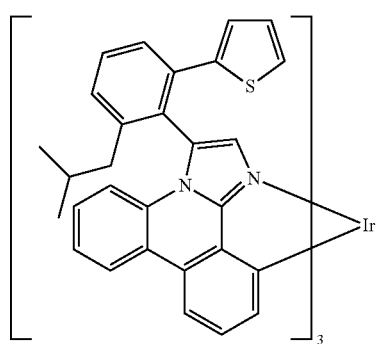
Compound 26
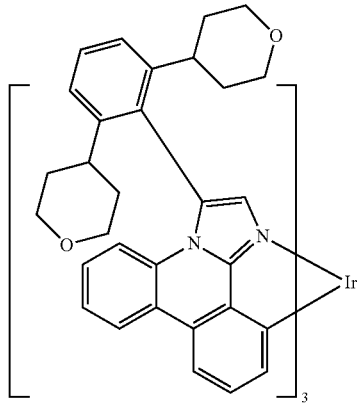
Compound 27
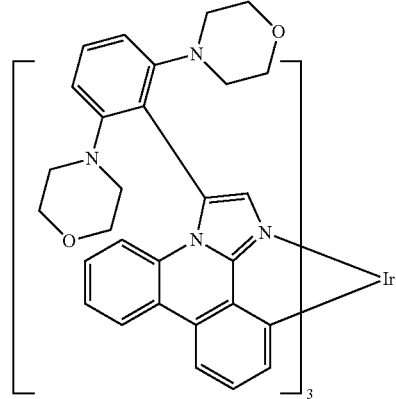
Compound 28
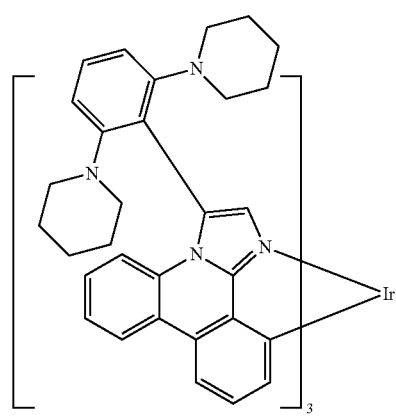

Compound 29
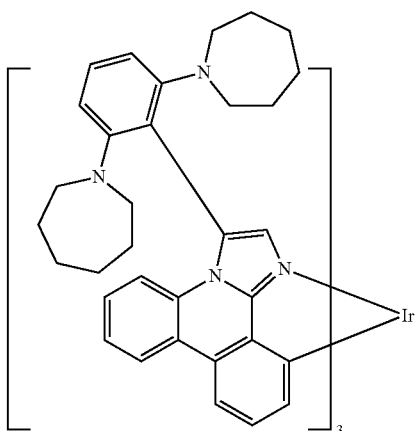
Compound 32
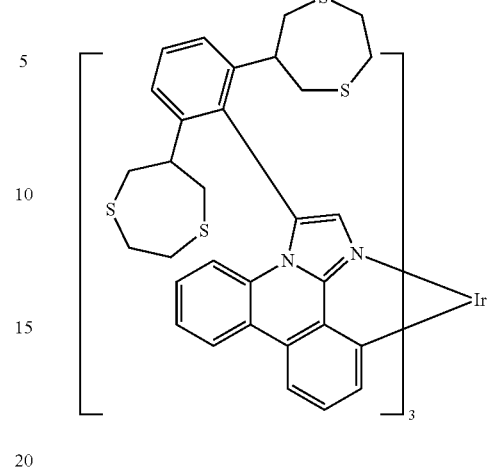
Compound 30
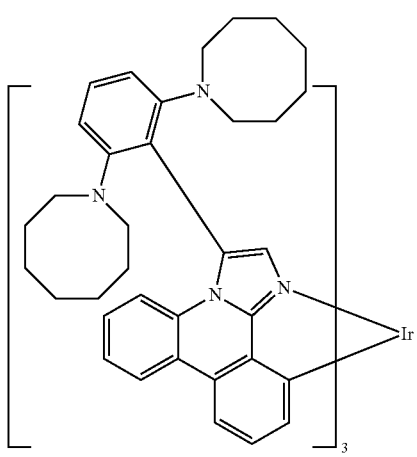
Compound 33
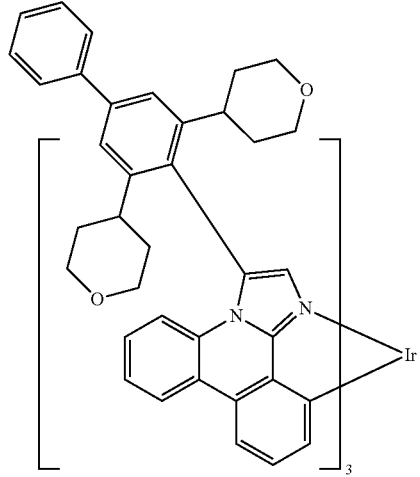
Compound 31
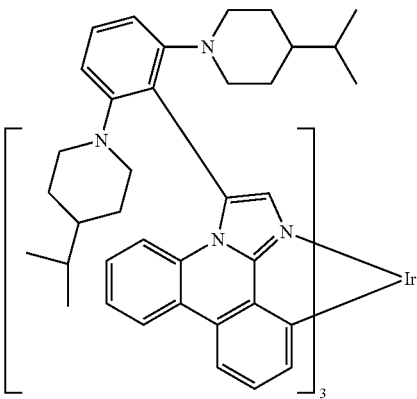
Compound 34
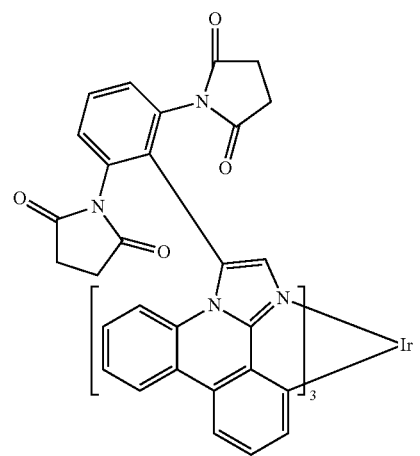

Compound 35

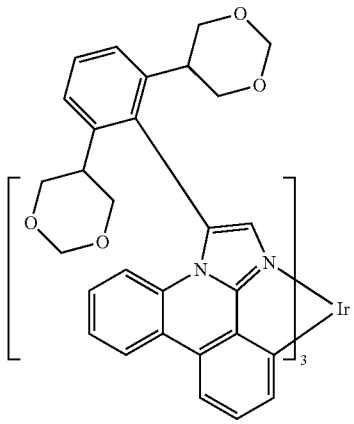

Compound 36

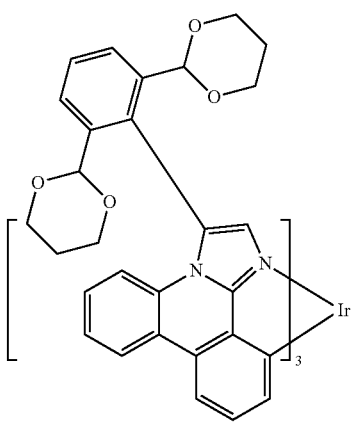

More preferably, the organic layer contains a compound selected from the group consisting of Compound 1 and Compound 2. Devices containing these compounds have been shown to have particularly good properties, such as high efficiency and long lifetime.

The organic layer may be an emissive layer in which the compound having FORMULA I is an emissive compound. The organic emissive layer may further comprise a host. Preferably, the host has the formula:

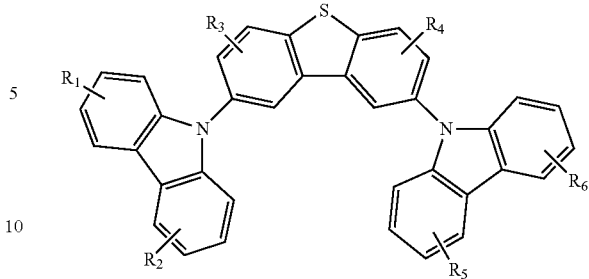

wherein each of $R_1$ through $R_6$ are independently selected from the group consisting of any alkyl, alkoxy, amino, alkenyl, alkynyl, arylkyl, aryl, heteroaryl and hydrogen, and where each of $R_1$ through $R_6$ may represent multiple substitutions.

A consumer product comprising a device is also provided, wherein the device further comprises an anode, a cathode and an organic layer. The organic layer further comprises a compounds having FORMULA I.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

| MATERIAL | EXAMPLES OF MATERIAL | PUBLICATIONS |
|---|---|---|
| Hole injection materials | | |
| Phthalocyanine and porphryin compounds | | Appl. Phys. Lett. 69, 2160 (1996) |

-continued

| MATERIAL | EXAMPLES OF MATERIAL | PUBLICATIONS |
| --- | --- | --- |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | $SO_3^-(H^+)$ | Synth. Met. 87, 171 (1997) |
| Arylamines complexed with metal oxides such as molybdenum and tungsten oxides | + $MoO_x$ | SID Symposium Digest, 37, 923 (2006) |

Hole transporting materials

| | | |
| --- | --- | --- |
| Triarylamines (e.g., TPD, α-NPD) | | Appl. Phys. Lett. 51, 913 (1987) |

| MATERIAL | EXAMPLES OF MATERIAL | PUBLICATIONS |
|---|---|---|
| | 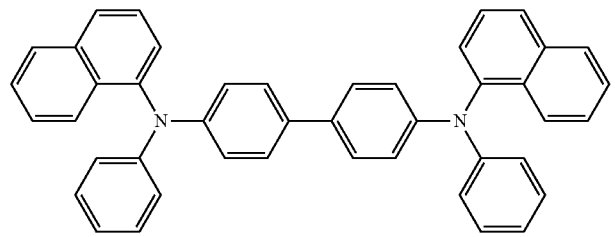 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 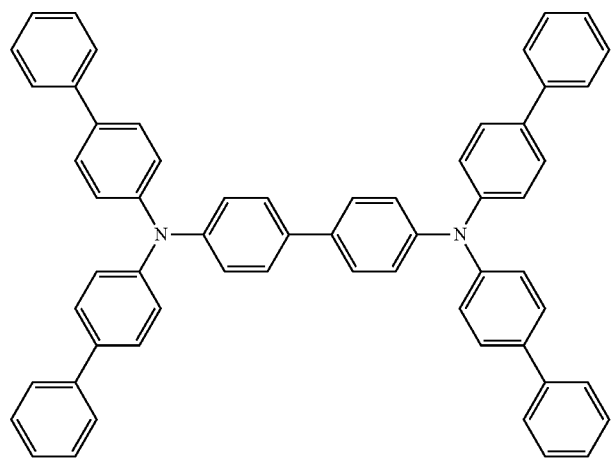 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 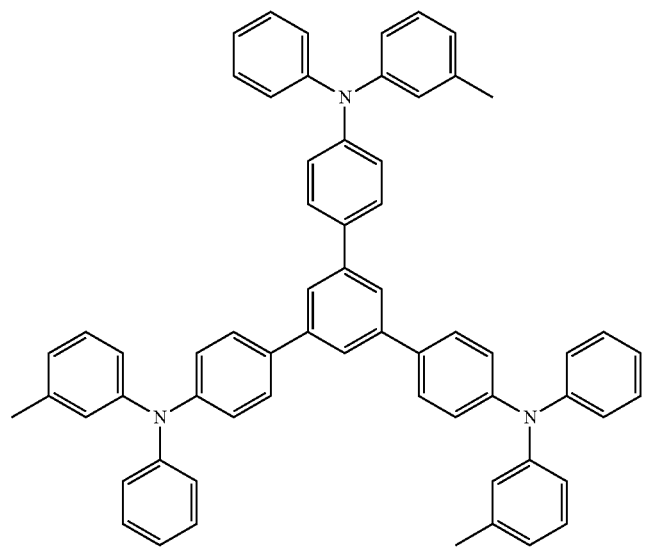 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994) |

| MATERIAL | EXAMPLES OF MATERIAL | PUBLICATIONS |
|---|---|---|
| Indolocarbazoles | | Synth. Met. 111, 421 (2000) |
| Isoindole compounds | | Chem. Mater. 15, 3148 (2003) |

Phosphorescent OLED host materials
Red hosts

| | | |
|---|---|---|
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |

| MATERIAL | EXAMPLES OF MATERIAL | PUBLICATIONS |
|---|---|---|
| | 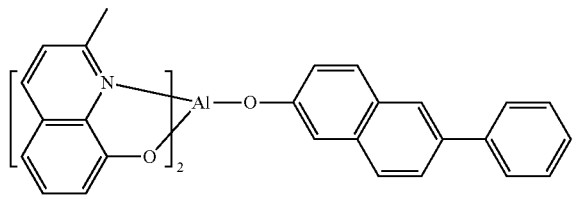 | WO200501455 |
| Metal phenoxybenzothiazole compounds | 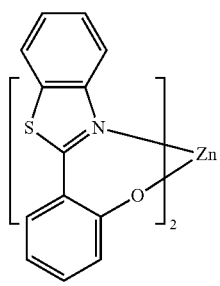 | Appl. Phys. Lett. 90, 123509 (2007) |
| Conjugated oligomers and polymers (e.g., polyfluorene) | 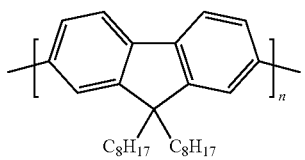 | Org. Electron. 1, 15 (2000) |
| Green hosts | | |
| Arylcarbazoles | 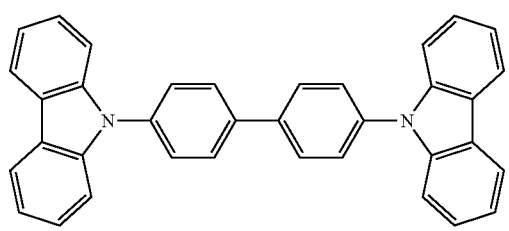 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 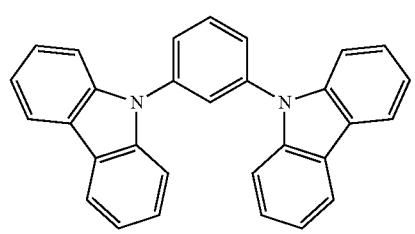 [SMILES: c1cc(-n2c3ccccc3c3ccccc32)cc(-n2c3ccccc3c3ccccc32)c1] | US2003175553 |
| | 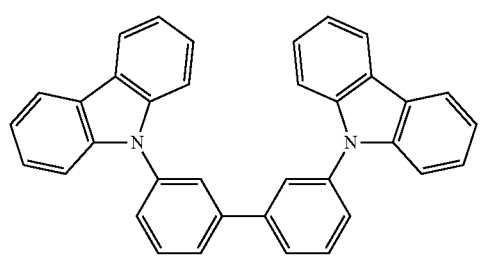 [SMILES: c1cc(-c2cccc(-n3c4ccccc4c4ccccc43)c2)cc(-n2c3ccccc3c3ccccc32)c1] | WO2001039234 |

| MATERIAL | EXAMPLES OF MATERIAL | PUBLICATIONS |
|---|---|---|
| Aryltriphenylene compounds | | US20060280965 |
| | | US20060280965 |
| Polymers (e.g., PVK) | | Appl. Phys. Lett. 77, 2280 (2000) |
| Spirofluorene compounds | | WO2004093207 |
| Metal phenoxybenzooxazole compounds | | WO05089025 |

| MATERIAL | EXAMPLES OF MATERIAL | PUBLICATIONS |
|---|---|---|
| | 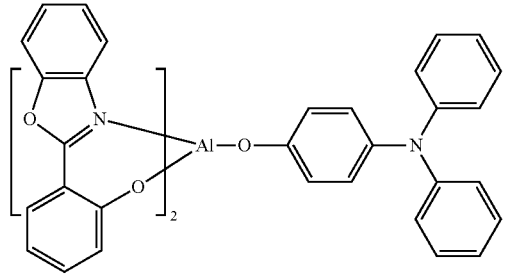 | WO06132173 |
| | 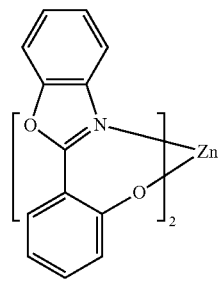 | JP200511610 |
| Spirofluorene-carbazole compounds | 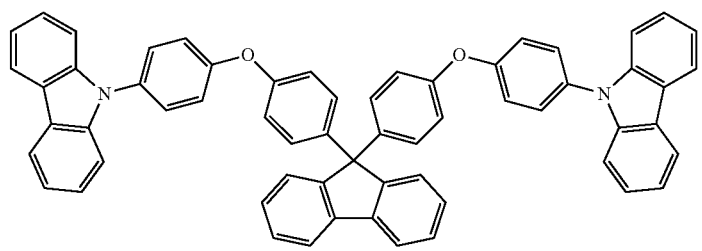 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
| | 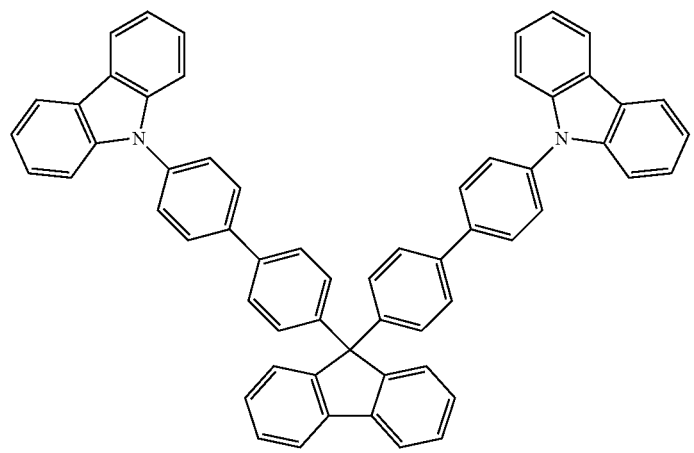 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 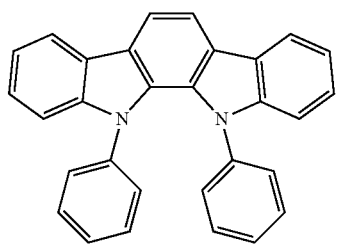 [SMILES: c1ccc(-n2c3ccccc3c3ccc4c5ccccc5n(-c5ccccc5)c4c32)cc1] | WO07063796 |

| MATERIAL | EXAMPLES OF MATERIAL | PUBLICATIONS |
|---|---|---|
| | | WO07063754 |
| 5-member ring electron deficient heterocycles (e.g., triazole, oxadiazole) | | J. Appl. Phys. 90, 5048 (2001) |
| | | WO04107822 |
| Metal phenoxypyridine compounds | | WO05030900 |

Blue hosts

| | | |
|---|---|---|
| Arylcarbazoles | | Appl. Phys. Lett, 82, 2422 (2003) |
| | | US20070190359 |

| MATERIAL | EXAMPLES OF MATERIAL | PUBLICATIONS |
|---|---|---|
| Dibenzothiopbene-carbazole compounds | | WO2006114966 |

Phosphorescent dopants
Red dopants

| | | |
|---|---|---|
| Heavy metal porphyrins (e.g., PtOEP) | | Nature 395, 151 (1998) |
| Iridium(III) organometallic complexes | | Appl. Phys. Lett. 78, 1622 (2001) |
| | | U.S. Pat. No. 06,835,469 |
| | | U.S. Pat. No. 06,835,469 |

| MATERIAL | EXAMPLES OF MATERIAL | PUBLICATIONS |
|---|---|---|
| | 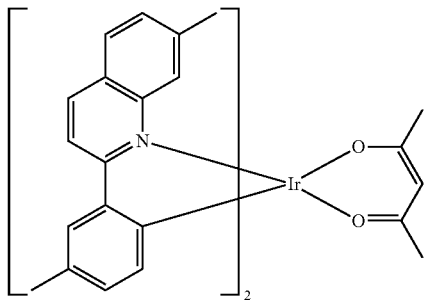 | US20060202194 |
| | 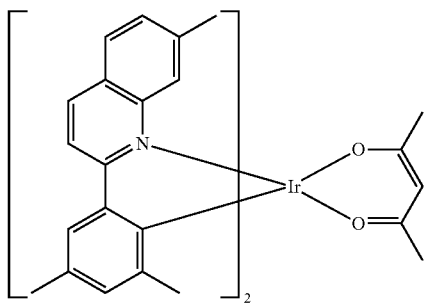 | US20060202194 |
| | 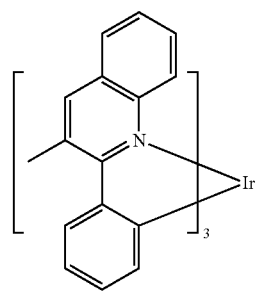 | U.S. Pat. No. 07,087,321 |
| | 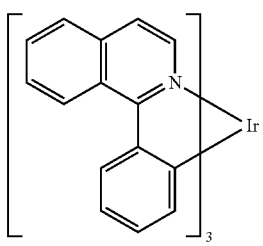 | U.S. Pat. No. 07,087,321 |
| | 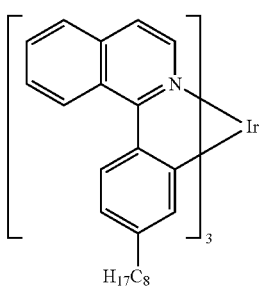 | Adv. Mater. 19, 739 (2007) |

| MATERIAL | EXAMPLES OF MATERIAL | PUBLICATIONS |
|---|---|---|
| Platinum(II) organotmetallic complexes | | WO2003040257 |
| Osminum(III) complexes | | Chem. Mater. 17, 3532 (2005) |
| Ruthenium(II) complexes | | Adv. Mater. 17, 1059 (2005) |
| Green dopants | | |
| Iridium(III) organometallic complexes | and its derivatives | Inorg. Chem. 40, 1704 (2001) |
| | | US2002034656 |

| MATERIAL | EXAMPLES OF MATERIAL | PUBLICATIONS |
| --- | --- | --- |
| | 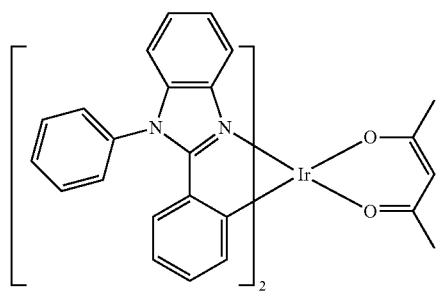 | U.S. Pat. No. 06,687,266 |
| | 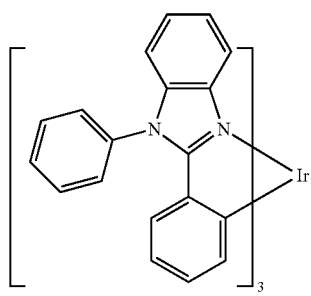 | Chem. Mater. 16, 2480 (2004) |
| | 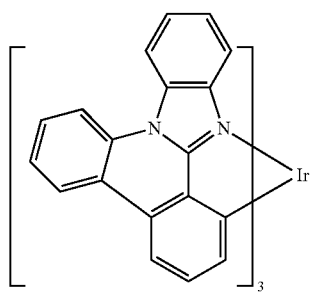 | US2007190359 |
| | 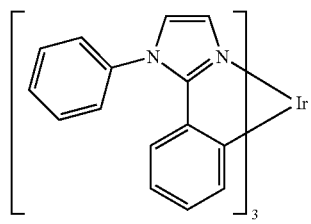 | US 2006008670 JP2007123392 |
| | 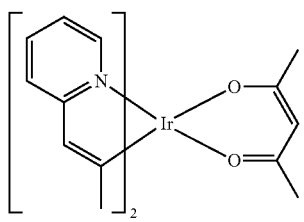 | Adv. Mater. 16, 2003 (2004) |

| MATERIAL | EXAMPLES OF MATERIAL | PUBLICATIONS |
|---|---|---|
| | 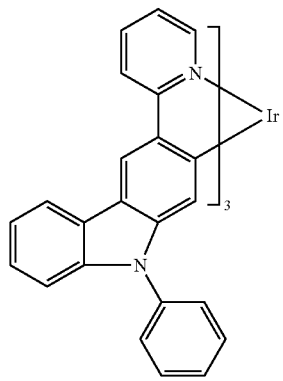 | Angew. Chem. Int. Ed. 2006, 45, 7800 |
| Pt(ll) organometallic complexes | 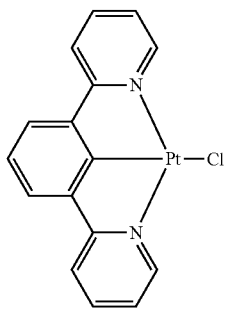 | Appl. Phys. Lett. 86, 153505 (2005) |
| | 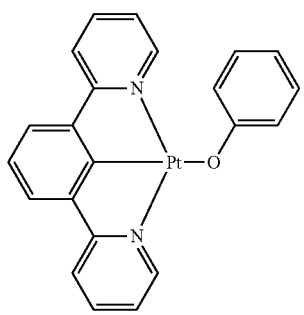 | Appl. Phys. Lett. 86, 153505 (2005) |
| | 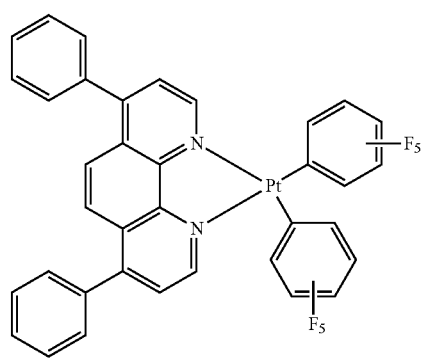 | Chem. Lett. 34, 592 (2005) |

| MATERIAL | EXAMPLES OF MATERIAL | PUBLICATIONS |
|---|---|---|
| Gold complexes | 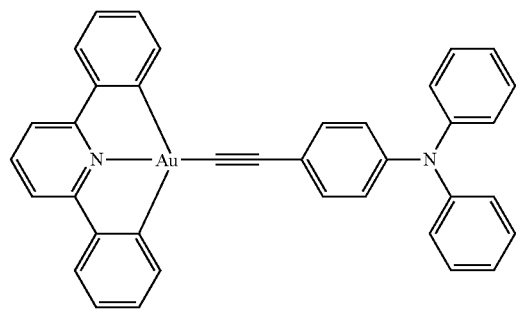 | Chem. Commun. 2906 (2005) |
| Rhenium(III) complexes | 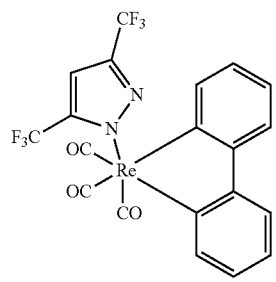 | Inorg. Chem. 42, 1248 (2003) |
| Blue dopants | | |
| Iridium(III) organometallic complexes | 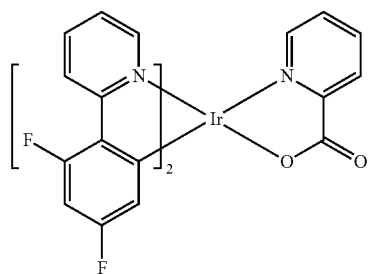 | WO2002002714 |
| | 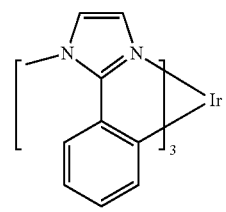 | WO2006009024 |
| | 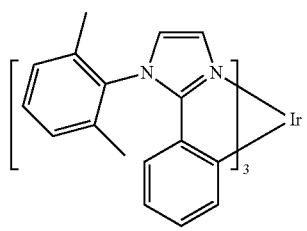 | US2006251923 |

| MATERIAL | EXAMPLES OF MATERIAL | PUBLICATIONS |
|---|---|---|
| | 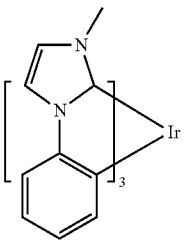 | WO2006056418, US2005260441 |
| | 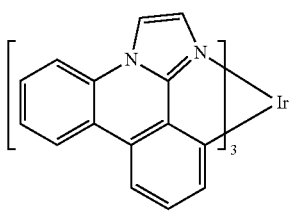 | US2007190359 |
| | 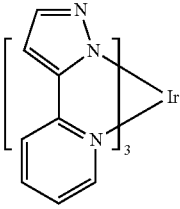 | US2002134984 |
| | 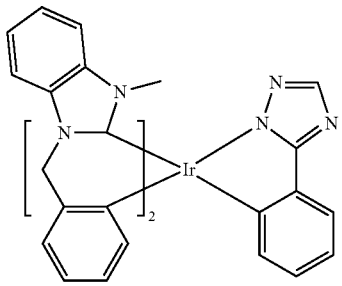 | Angew. Chem. Int. Ed. 47, 1 (2008) |
| | 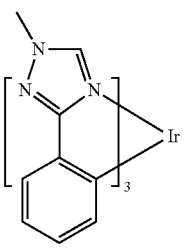 | Chem. Mater. 18, 5119 (2006) |
| | 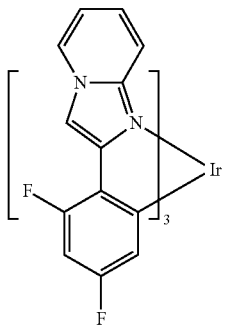 | Inorg. Chem. 46, 4308 (2007) |

| MATERIAL | EXAMPLES OF MATERIAL | PUBLICATIONS |
|---|---|---|
| | 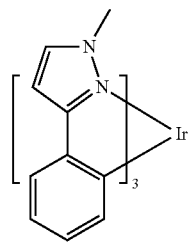 | WO05123873 |
| | 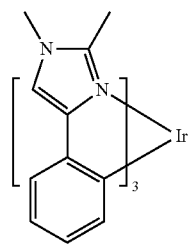 | WO05123873 |
| | 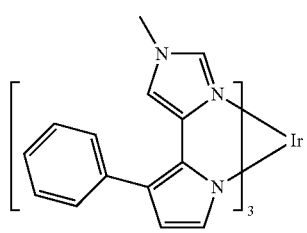 | WO07004380 |
| | 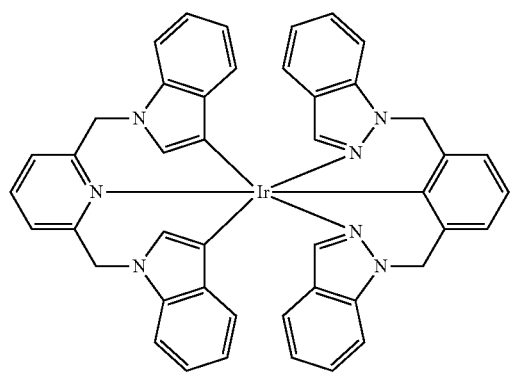 | WO06082742 |
| Osmium(II) complexes | 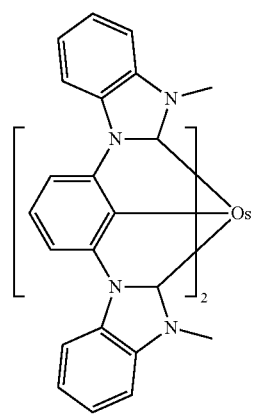 | US2005260449 |

| MATERIAL | EXAMPLES OF MATERIAL | PUBLICATIONS |
|---|---|---|
| | 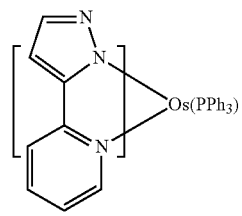 | Organometallics 23, 3745 (2004) |
| Gold complexes | 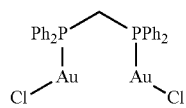 | Appl. Phys. Lett. 74, 1361 (1999) |
| Platinum(II) complexes | 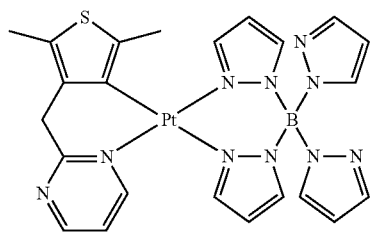 | WO06098120, WO06103874 |
Exciton/hole blocking layer materials
| | | |
|---|---|---|
| Bathocuprine compounds (e.g., BCP, BPhen) | 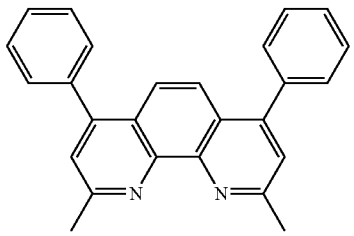 [SMILES: Cc1cc(-c2ccccc2)c2ccc3c(-c4ccccc4)cc(C)nc3c2n1] | Appl. Phys. Lett. 75, 4 (1999) |
| | 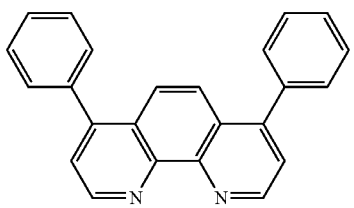 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 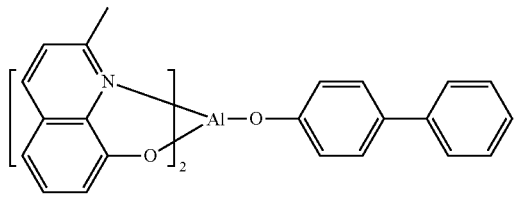 | Appl. Phys. Lett. 81, 162 (2002) |

| MATERIAL | EXAMPLES OF MATERIAL | PUBLICATIONS |
|---|---|---|
| 5-member ring electron deficient heterocycles such as triazole, oxadiazole, imidazole, benzoimidaxole | 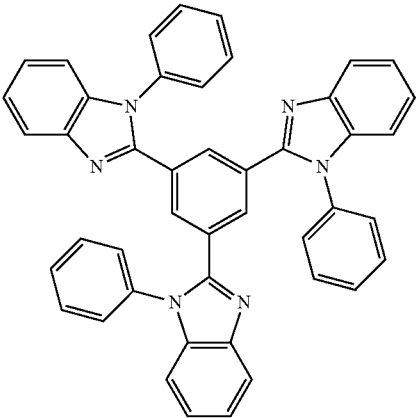 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 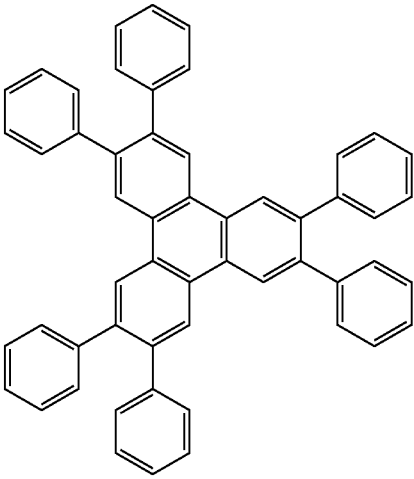 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | U320050025993 |
| Fluorinated aromatic compounds | 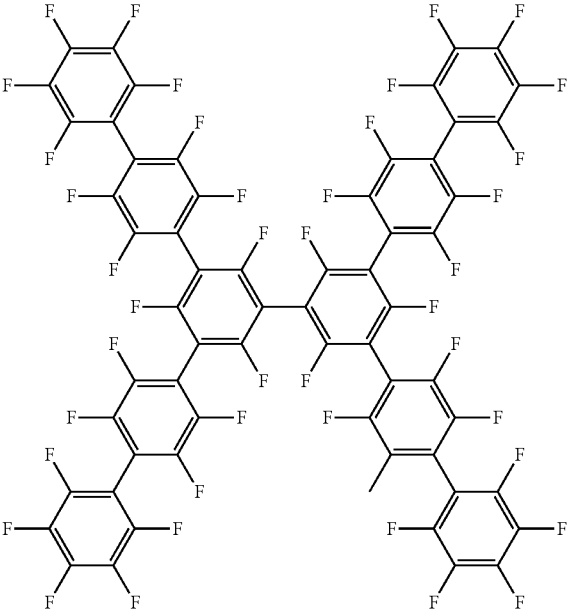 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |

-continued
| MATERIAL | EXAMPLES OF MATERIAL | PUBLICATIONS |
|---|---|---|
| Electron transporting materials | | |
| Anthracene-benzoimidazole compounds | 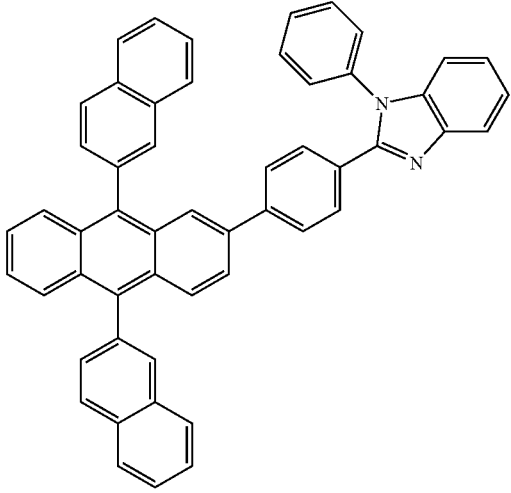 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO03060956 |
| Anthracene-benzothiazole compounds | 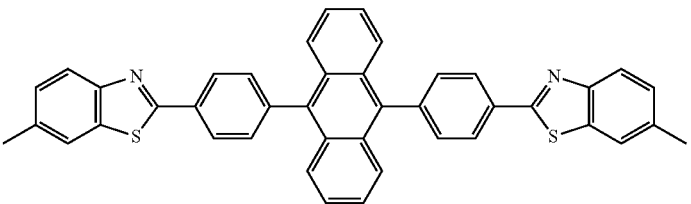 | Appl. Phys. Lett. 89, 063504 (2006) |
| Metal 8-hydroxyquinolates (e.g., Alq₃) | 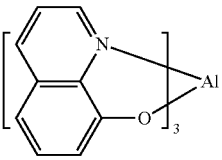 | Appl. Phys. Lett. 51, 913 (1987) |
| Metal hydroxy-benoquinolates | 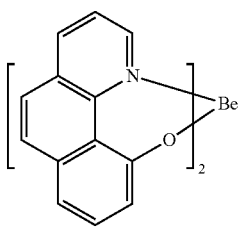 | Chem. Lett. 5, 905 (1993) |
| Bathocuprine compounds such as BCP, BPhen, etc | 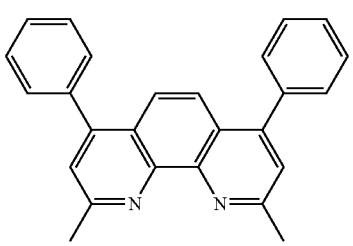 [SMILES: Cc1cc(-c2ccccc2)c2ccc3c(-c4ccccc4)cc(C)nc3c2n1] | Appl. Phys. Lett. 91, 263503 (2007) |
| | 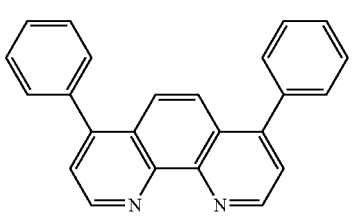 [SMILES: c1ccc(-c2ccnc3c2ccc2c(-c4ccccc4)ccnc23)cc1] | Appl. Phys. Lett. 79, 449 (2001) |

| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 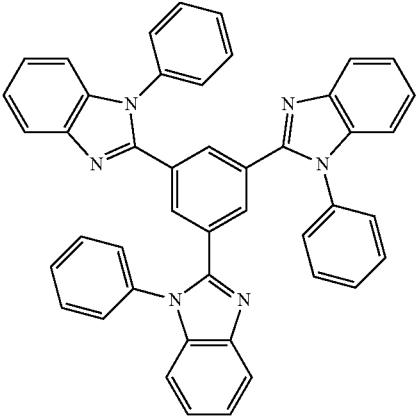 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 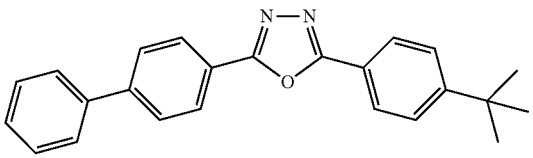 [SMILES: CC(C)(C)c1ccc(-c2nnc(-c3ccc(-c4ccccc4)cc3)o2)cc1] | Appl. Phys. Lett. 55, 1489 (1989) |
| | 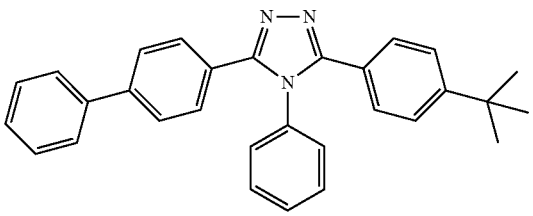 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 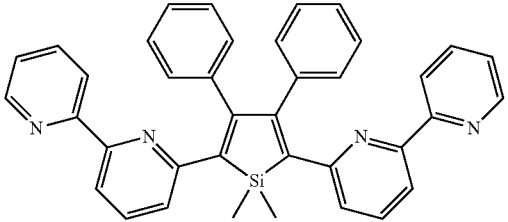 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 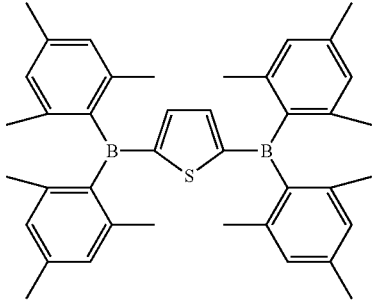 | J. Am. Chem. Soc. 120, 9714 (1998) |
| Fluorinated aromatic compounds | 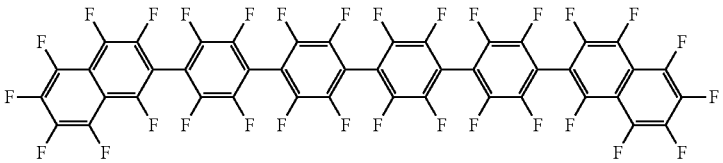 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

EXPERIMENTAL

Compound Examples

Synthesis of Comparative Example 2

Step 1

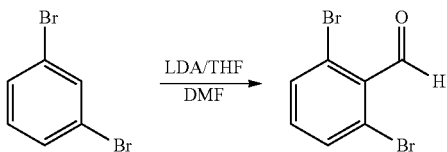

Into a 1000 mL 3-neck flask equipped with magnetic stirring, a condenser and a thermocouple was charged with 100 mL of 2.0 M Lithium diisopropylamide (LDA) in THF. This solution was cooled to −75° C. Next, 1,3-Dibromobenzene (39.3 g, 0.167 mol) dissolved in 200 mL of anhydrous THF was added dropwise over a ½ h period to the cooled solution of LDA. The internal temperature was maintained at −75° C. (+/−5° C.) for 2 h. Next, dimethylformamide (30.8 g, 0.4 mol) dissolved in 50 mL of anhydrous THF and was added dropwise to the cooled reaction mixture over a ½ h period. The internal temperature was maintained at −75° C. (+/−5° C.) for 2 h. The reaction mixture was quenched by dropwise addition of 100 mL of 5% sulfuric acid. The cooling bath was removed and the reaction mixture was allowed to warm to room temperature. The organic layer was separated and the aqueous was extracted with 1×100 mL of diethyl ether and 1×50 mL of ethyl acetate. The organics were combined and washed 1×100 mL of brine. The organic extracts were then dried over sodium sulfate, filtered and concentrated under vacuum. The crude product was recrystallized from hexanes to yield 21.6 g (49% yield) of product.

Step 2

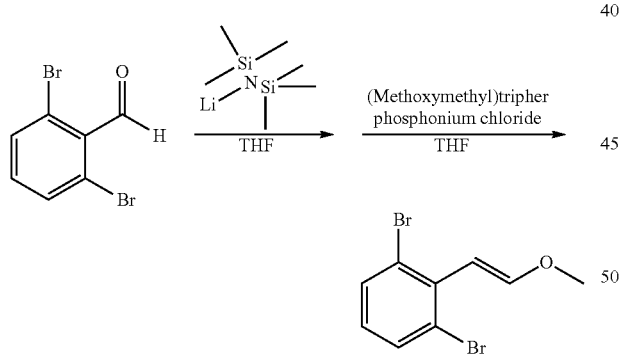

(Methoxymethyl)triphenylphosphonium chloride (34.3 g, 0.10 mol) was charged into a 500 mL 3-neck flask with 75 mL of THF. This solution was cooled to −78° C. followed by dropwise addition of 100 mL (0.1 mol) of 1.0 M of lithium bis(trimethylsilyl)amide in THF. Addition time was approximately 20 minutes and the internal temperature was maintained at −78° C. to −70° C. The cooling bath was then removed and the reaction mixture was allowed to warm to 0 to 3° C. The reaction mixture was then cooled back down to −78° C. Next, 2,6-dibromobenzaldehyde (22.8 g, 0.086 mol) dissolved in 75 mL of THF was added dropwise to the cooled reaction mixture over a 20 min period. The internal temperature was maintained between −78° C. to −70° C. The reaction mixture was then allowed to gradually warm to room temperature. The reaction mixture was quenched with aqueous ammonium chloride and then extracted with 3×300 mL of ethyl acetate. The organic extracts were combined, washed once with 200 mL of 10% LiCl solution and were dried over magnesium sulfate. The extracts were then filtered and the solvent removed under vacuum. The crude product was purified by vacuum distillation to yield 22.5 g (90%) of product as a light-orange oil.

Step 3

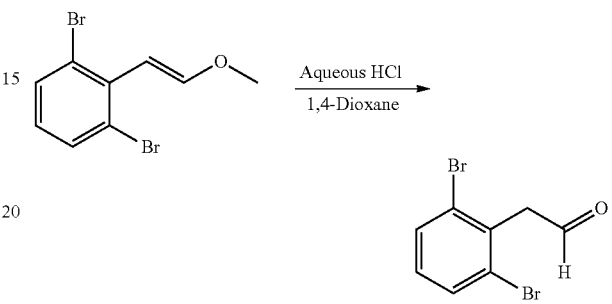

70 mL of conc. HCl was slowly added to a 500 mL round bottom flask containing 110 mL of water. o-Methyl 2,6-dibromophenylacetaldehyde (22.5 g, 0.077 mol) was dissolved in 70 mL of 1,4-dioxane and this solution was added all at once to the 500 mL round bottom flask. The reaction mixture was stirred and heated at a gentle reflux for 18 h. The reaction mixture was cooled to room temperature and was extracted with 2×400 mL ethyl acetate. These extracts were combined and were washed with 1×100 mL aq. 10% LiCl. The extracts were then dried over sodium sulfate, filtered and the solvent removed under vacuum. The 2,6-dibromophenyl acetaldehyde was purified using silica gel chromatography with 15%/75% methylene chloride/hexanes as the eluent. 17.1 g (80% yield) of white solids was obtained as the product.

Step 4

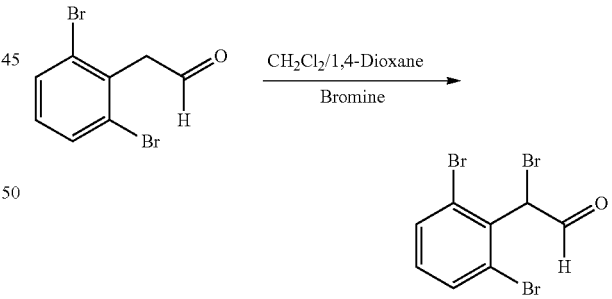

To a 200 mL round bottom flask was added 3.75 g (0.013 mol) of the 2,6-dibromophenylacetaldehyde, 30 mL of methylene chloride and 60 mL of 1,4-dioxane. Next, 2.32 g, (0.014 mol) of bromine was dissolved in 30 mL of methylene chloride and was added dropwise to the reaction mixture at room temperature over a 10 min period. Stirring was continued at room temperature for 2 h. An additional (0.23 g, 0.001 mol) of bromine was added to the reaction mixture. This mixture was stirred for one hour at room temperature. The reaction mixture was concentrated under vacuum. The crude product was then dissolved in 50 mL of diethyl ether and was washed 1×50 mL aqueous sodium bisulfite and 1×50 mL aqueous 10% lithium chloride. The ethereal extract was dried over sodium sulfate then was filtered and the solvent removed under vacuum to yield 4.2 g (90% yield) of a yellow viscous oil as the product which was immediately used for the next step.
Step 5

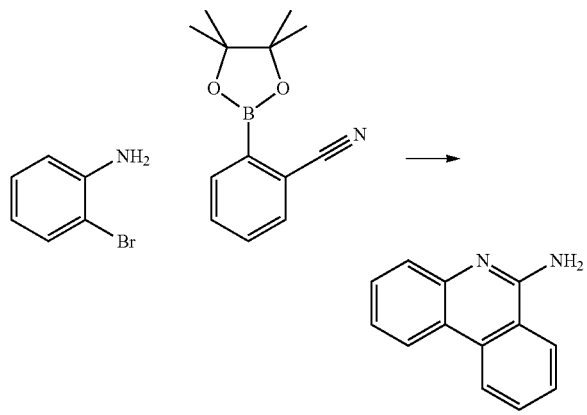

To a 1 L 3-neck flask was added 19 g (0.11 mol) of 2-bromoaniline, 27.7 g (0.12 mol) of 2-cyanophenylboronic acid pinacol ester, 74.5 g (0.32 mol) of potassium phosphate tribasic monohydrate and 1.8 g (0.002 mol) of [1,1'-bis[(diphenylphosphino)ferrocene]dichoro-palladium(II) complex with dichloromethane(1:1). This mixture was degassed and backfilled with nitrogen. Next, water (13 mL) and 350 mL of 1,4-dioxane were added to the reaction mixture and the degassing procedure was repeated. The reaction mixture was stirred and heated under nitrogen at reflux for 18 h. After cooling, the reaction mixture was diluted with 350 mL of water. The reaction mixture was extracted with 3×250 mL of ethyl acetate. These extracts were combined and dried over magnesium sulfate. The extracts were filtered and the solvent removed under vacuum. The crude product was triturated with a hexane/ethyl acetate mixture. A light gray solid was isolated via filtration.

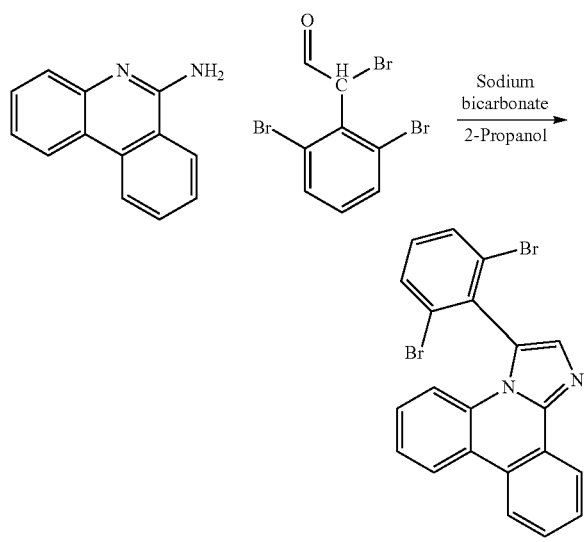

A 200 mL round bottom flask was charged with 0.77 g (0.004 mol) of 6-aminophenanthridine and 50 mL of anhydrous 2-propanol. To this mixture was added 1.42 g (0.004 mol) of α-bromo-2,6-dibromophenylacetaldehyde all at once. This mixture was then heated at reflux for 24 h. Next, the reaction mixture was cooled to 60° C. and 0.67 g (0.008 mol) of sodium bicarbonate was added all at once. This mixture was then heated at reflux for 24 h. The reaction mixture was cooled to room temperature, diluted with 300 mL of water and then was extracted with 3×200 mL of ethyl acetate. These organic extracts were combined, were washed 1×100 mL of aqueous 10% LiCl, were dried over sodium sulfate, then were filtered and concentrated under vacuum. The crude product was purified by silica gel column chromatography (1-7% ethyl acetate/methylene) to yield 1 g (55% yield) of off-white solids as the product.
Step 7

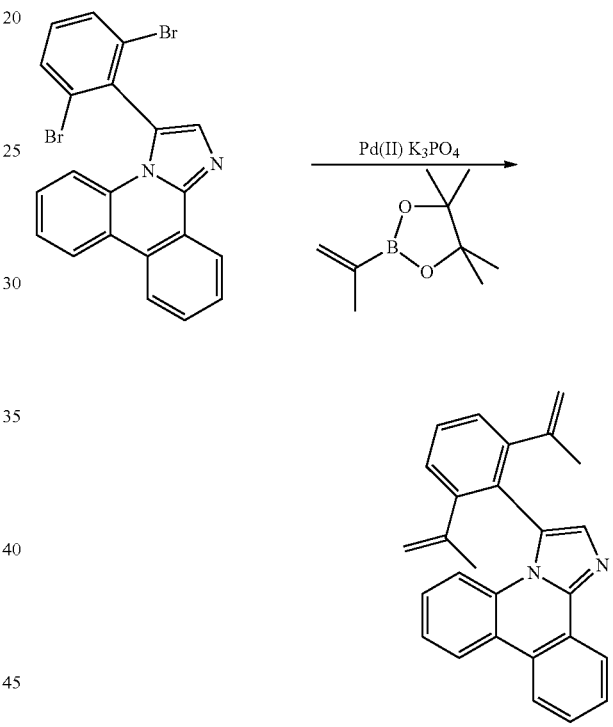

To a 200 mL flask was added dibromide from Step 6 (2.34 g, 5.175 mmol), isopropenyl boronic acid pinacol ester (10.44 g, 62.1 mmol), palladium(II) acetate (0.17 g, 0.76 mmol), 2-dicyclohexylphosphino-2',6'-dimethoxybiphenyl (0.62 g, 1.52 mmol), potassium phosphate tribasic monohydrate (5.96 g, 25.88 mmol), 122 mL of toluene and 122 mL of water. The reaction mixture was fully degassed by freezing-pump-thaw technique. The reaction was heated to reflux and stirred under a nitrogen atmosphere for 16 h. The reaction mixture was filtered through a pad of Celite. The toluene layer was separated and the aqueous was extracted once with 75 mL of toluene. The toluene extracts were combined, dried over sodium sulfate, then were filtered and concentrated under vacuum. The product was purified using silica gel chromatography with 1-8% ethyl acetate/methylene chloride as the eluent to give 1.7 g (87% yield) of product.

Step 8

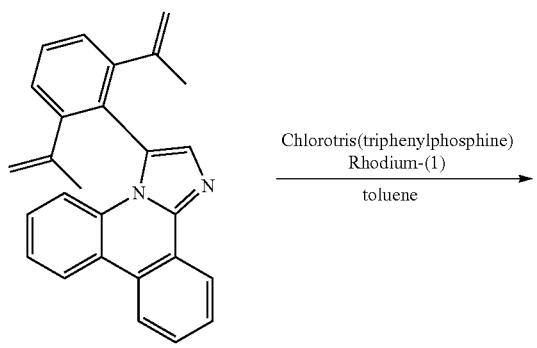

2,6-diisopropenylimidazophenanthridine (1.7 g, 4.6 mmol) was dissolved in 75 mL of toluene. This solution was added to a Parr hydrogenator vessel that was purged with N₂ and contained 1.5 g of chlorotris(triphenylphosphine) rhodium(I). This vessel was placed on the Parr hydrogenator and the vessel was filled with hydrogen and evacuated (repeated a total of three times). The vessel was then filled with hydrogen to 45 psi. This mixture was reacted with shaking for 21 h. The solvent from the reaction mixture was removed under vacuum. The crude product was chromatographed using a silica gel column with 1-8% ethyl acetate/methylene chloride as the eluent to yield 1.65 g of product.

Step 9

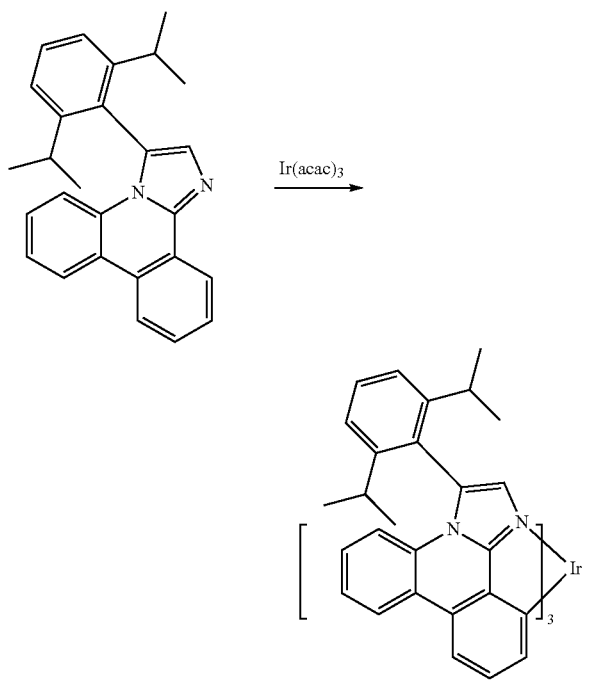

Comparative Example 2

To a 50 mL Schlenk tube was added the ligand from Step 8 (1.47 g, 3.88 mmol), Ir(acac)$_3$ (0.38 g, 0.78 mmol) and tridecane (50 drops). The mixture was degassed and heated in a sand bath at 240° C.-250° C. with stirring under a nitrogen for 66 h. After cooling, the reaction mixture was dissolved with a mixture of solvent (CH$_2$Cl$_2$:hexanes=1:1) and subject to flash column chromatography with 1:1 CH$_2$Cl$_2$:hexanes as the eluent. The solid after column chromatography was recrystallized from a mixture of CH$_2$Cl$_2$ and methanol to yield 0.65 g (65%) of product.

Synthesis of Compound 1

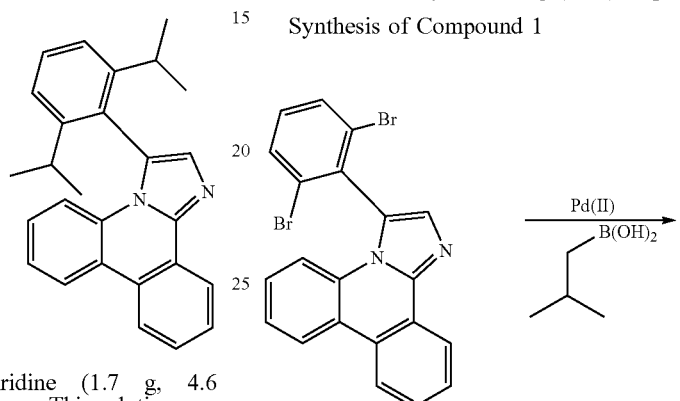

Step 1:

To a 200 mL flask was added dibromide (1.0 g, 2.2 mmol), isobutyl boronic acid (2.7 g, 26.5 mmol), Pd$_2$(dba)$_3$ (0.15 g, 0.16 mmol), 2-dicyclohexylphosphino-2',6'-dimethoxybiphenyl (0.27 g, 0.65 mmol), potassium phosphate tribasic monohydrate (8.7 g, 37.58 mmol) and 100 mL of toluene. The reaction mixture was fully degassed by freezing-pump-thaw technique. The reaction was heated to reflux and stirred under a nitrogen atmosphere for 16 h. The reaction mixture was filtered through a pad of Celite. The toluene layer was separated and the aqueous was extracted once with 75 mL of toluene. The toluene extracts were combined, dried over sodium sulfate, then were filtered and concentrated under vacuum. The product was purified using silica gel chromatography with 1-8% ethyl acetate/methylene chloride as the eluent to give 0.76 g of product (84% yield).

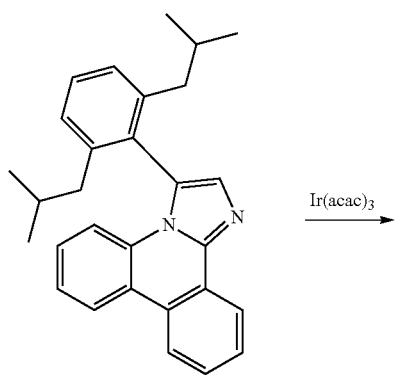

Ir(acac)₃

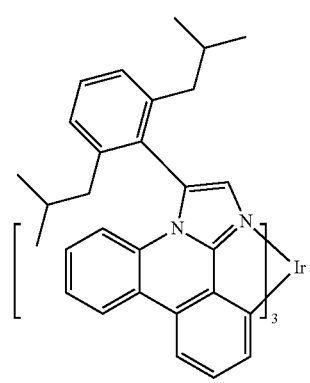

Compound 1

Step 2:

To a 50 mL Schlenk tube was added the ligand (2.8 g, 6.89 mmol), Ir(acac)₃ (0.68 g, 1.38 mmol) and tridecane (50 drops). The mixture was degassed and heated in a sand bath at 240-250° C. with stirring under a nitrogen for 73 h. After cooling, the reaction mixture was dissolved with a mixture of solvent (CH₂Cl₂:hexanes=1:1) and subject to flash column chromatography with 1:1 CH₂Cl₂:hexanes as the eluent. The solid after column chromatography was recrystallized from a mixture of CH₂Cl₂ and methanol to yield 1.69 g (87%) of product.

Synthesis of Compound 2

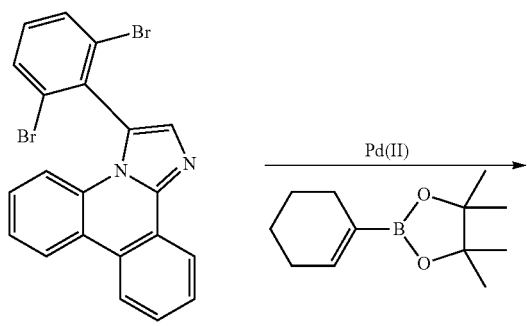

Pd(II)

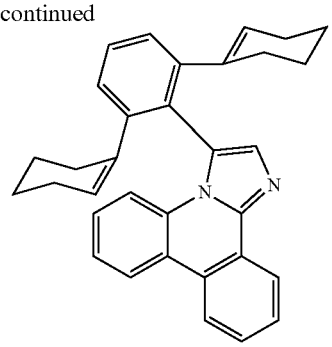

Step 1:

To a 200 mL flask was added the dibromide (4 g, 8.84 mmol), 1-cyclohexene boronic acid pinacol ester (18.37 g, 88.27 mmol), Pd(OAc)₂ (1.98 g, 2.9 mmol), 2-dicyclohexylphosphino-2',6'-dimethoxybiphenyl (2.4 g, 5.83 mmol), potassium phosphate tribasic monohydrate (10.18 g, 44.23 mmol), 100 mL of toluene and 100 mL of water. The reaction mixture was fully degassed by freezing-pump-thaw technique. The reaction was heated to reflux and stirred under a nitrogen atmosphere for 16 h. The reaction mixture was filtered through a pad of Celite. The toluene layer was separated from the filtrate. The aqueous layer was extracted with 75 mL of toluene. The toluene extracts were combined, dried over sodium sulfate, then were filtered and concentrated under vacuum. The crude product was purified by column chromatography with 1-4% ethyl acetate/methylene chloride as the eluent to yield 3.2 g of product.

Pt/C, Pd/C, H₂

Step 2:

3.2 g (0.007 mol) of the cyclohexenyl compound was dissolved in 150 mL of toluene. This solution was added to a Parr hydrogenation vessel that was purged with nitrogen and was charged with 2.8 g of 10% palladium on activated carbon and 1.4 g of platinum, 5 wt % (dry basis) on activated carbon wet, Degussa type F101. This heterogeneous mixture was shaken on the Parr hydrogenator for 72 h. The reaction mixture was filtered through a pad of Celite. The toluene filtrate was concentrated under vacuum. The crude product was purified by column chromatography with 1-5% ethyl acetate/methylene chloride as the eluent to yield 3.1 g of product.

Compound 2

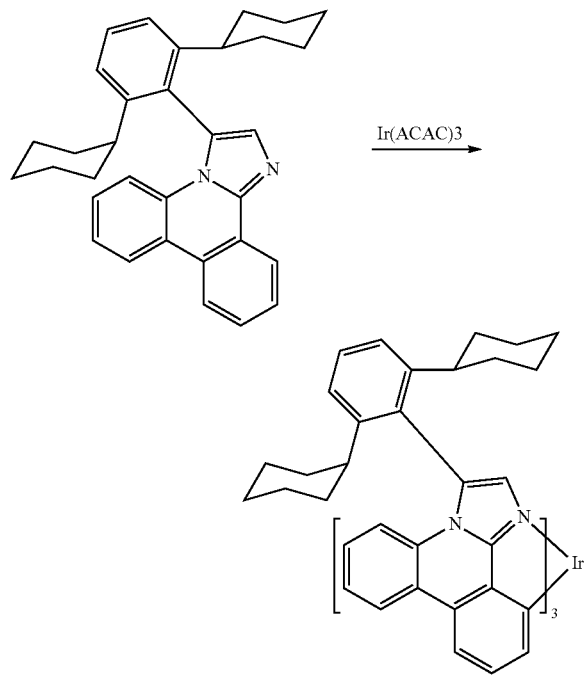

Step 3:
To a 50 mL Schlenk tube were added ligand (2.3 g, 5.08 mmol), Ir(acac)₃ (0.5 g, 1.01 mmol and tridecane (50 drops). The mixture was degassed and heated in a sand bath with stirring under a nitrogen for 73 h. After cooling, the reaction mixture was dissolved with a mixture of solvent (CH$_2$Cl$_2$: hexanes=1:1) and subject to flash column chromatography with 1:1 CH$_2$Cl$_2$:hexanes as the eluent. The solid after column chromatography was recrystallized from a mixture of CH$_2$Cl$_2$ and methanol to yield 0.93 g (58%) of product.

Synthesis of Compound 3

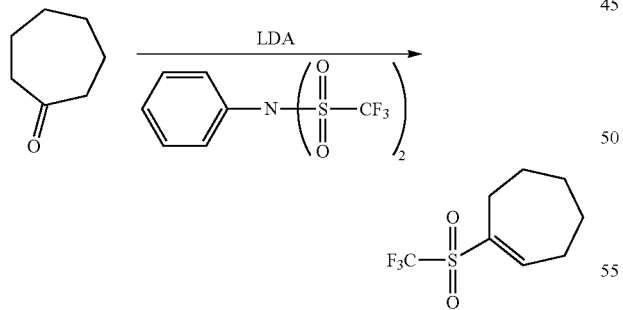

Step 1.
To a 500 mL 3-neck flask was charged diisopropylamine (9.9 g, 0.098 mol) and 100 mL of THF. This solution was cooled to −78° C. and 45.6 mL, 0.073 mol of n-BuLi 1.6 M in hexanes were added to the cooled reaction mixture via syringe. This mixture was stirred for ½ h at −78° C., then cycloheptanone (6.0 g, 0.054 mol) in 30 mL of THF was added dropwise to the cooled reaction mixture. This solution was stirred at −78° C. for 2 h. A THF solution of N-phenyl-bis-trifluoromethane sulfoimide (21.2 g, 0.059 mol) was added dropwise to the cooled mixture. The mixture was then allowed to gradually warm to room temperature and was stirred overnight. The reaction mixture was quenched with aqueous ammonium chloride then was extracted 2×300 mL of ethyl acetate. The extracts were then dried over magnesium sulfate and were filtered and concentrated under vacuum. The crude product was chromatographed with 30-40% methylene chloride/hexanes as the eluent to yield 9.0 g (69% yield) of product.

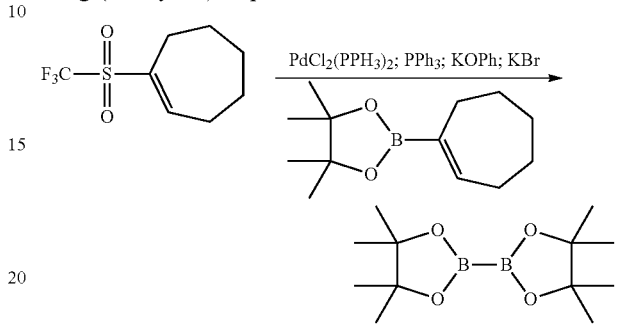

Step 2.
PdCl$_2$(PPh$_3$)$_2$ (1.722 g, 2.45 mmol), PPh$_3$ (1.28 g, 4.9 mmol), bis(pinacolato)diboron (90.76 g, 357 mmol) and KOPh (16.2 g, 122.7 mmol) were added to a flask. The flask was flushed with nitrogen and then charged with toluene (300 mL) and the triflate (20 g, 81.8 mmol). The mixture was then stirred at 50° C. for 16 h. The reaction mixture was diluted with 200 mL of water. The toluene layer was separated. The aqueous layer was extracted 200 mL of toluene. The toluene extracts were combined, washed 100 mL of aqueous 10% lithium chloride, dried over magnesium sulfate, filtered and concentrated under vacuum. The crude product was distilled using a Kugelrohr distillation setup. The pot temperature was started at 85° C. and was increased to 115° C. This distilled mixture was chromatographed with 20-25% methylene chloride/hexanes as the eluent to yield 9.85 g (55% yield) of product.

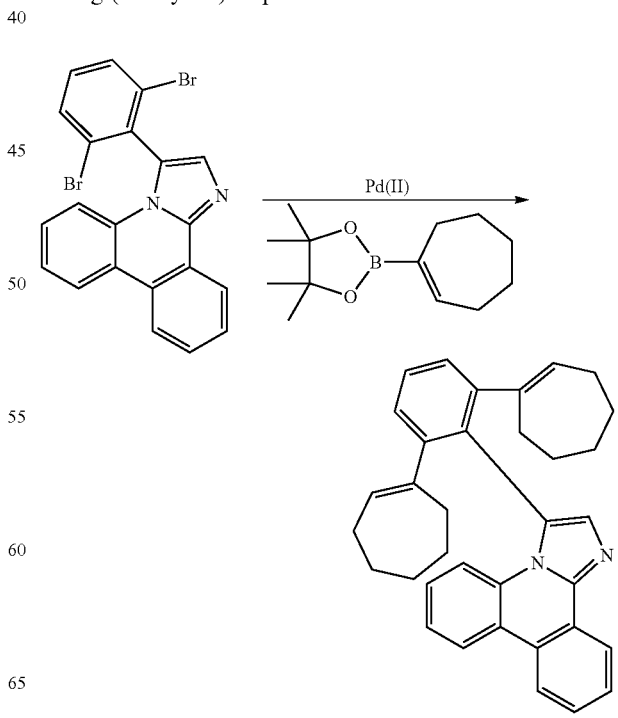

Step 3.

To a 500 mL round bottom flask was added the dibromide (4.7 g, 0.01 mol), the boronic acid pinacol ester (9.81 g, 0.0442 mol), Pd(OAc)$_2$ (0.75 g, 0.0033 mol), dicyclohexylphosphino-2',6'-dimethoxybiphenyl (2.73 g, 0.007 mol), potassium phosphate tribasic monohydrate (12.0 g, 0.052 mol), 200 mL of toluene and 75 mL of water. The reaction mixture was evacuated and back-filled with nitrogen. The reaction was then heated to reflux and stirred under a nitrogen atmosphere for 16 h. The mixture was filtered through a pad of Celite. The toluene layer was separated and the aqueous was extracted with 100 mL of toluene. The toluene portions were combined and dried over magnesium sulfate. This dried organic mixture was then filtered and concentrated under vacuum. The crude product was purified by silica gel chromatography. The first purification involved eluting the column with 1-4% ethyl acetate/methylene chloride. The second purification involved eluting the column with 2-12% ethyl acetate/hexanes. The yield was 4.1 g (82%).

These extracts were dried over magnesium sulfate then were filtered and concentrated under vacuum. These extracts were then passed through a neutral alumina (deactivated by the addition of 6% (w/w) water) column that was eluted with 20-70% methylene chloride/hexanes. The material was dissolved in 50 mL of methylene chloride and was stirred at room temperature for 18 h with 0.8 g of Si-TAAcoH and 0.8 g of Si-Thiourea. This mixture was then filtered, concentrated under vacuum and the resulting material was recrystallized from hexanes to yield 2.93 g (71% yield) of product.

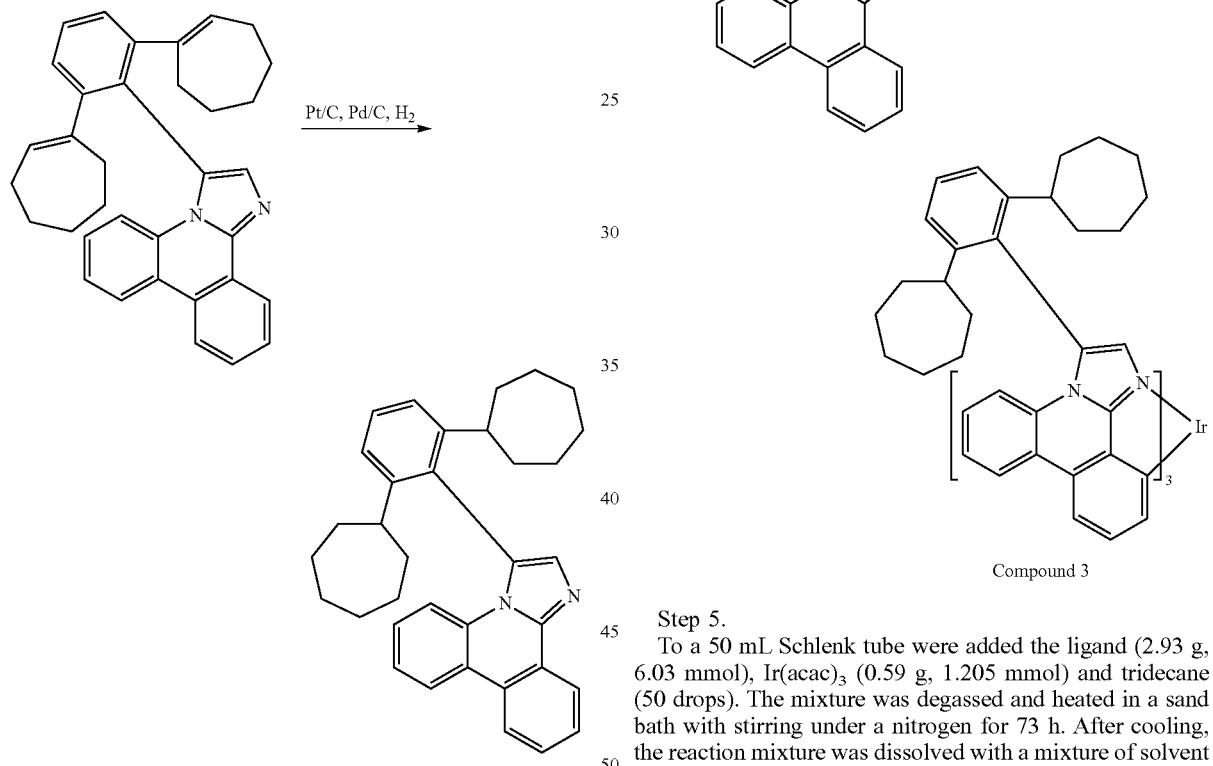

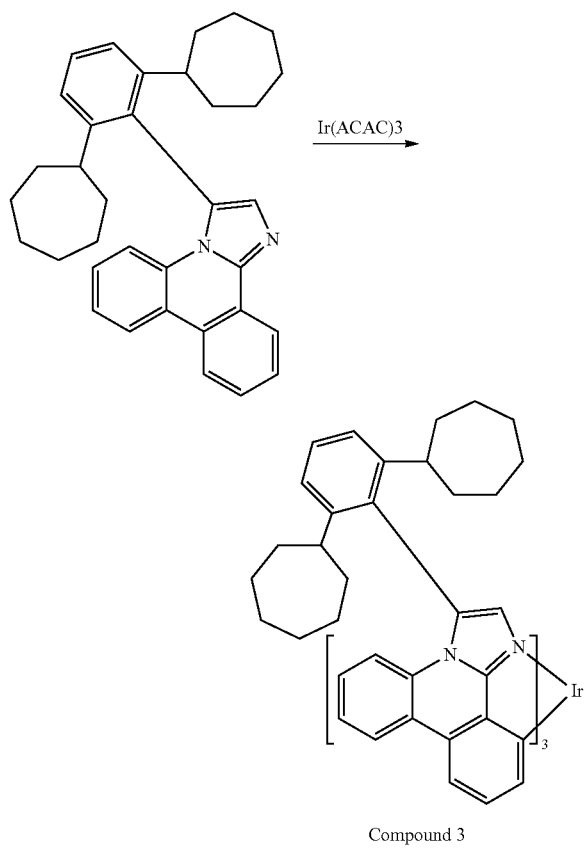

Step 4.

The alkenyl product from Step 3 was dissolved in 200 mL of toluene and was charged into a Parr hydrogenation bottle containing 2.8 g of 10% Pd/C and 1.4 g of 5% Pt/C Degussa Type F101 RA/W. This mixture was placed on the Parr hydrogenator for 18 h. The reaction mixture was filtered through a pad of Celite and the pad was rinsed with 200 mL of toluene. The toluene filtrate was concentrated under vacuum. The crude product was purified by silica gel chromatography with 5-15% ethyl acetate/hexanes as the eluent. The product obtained (3.6 g, 0.0074 mol) was dissolved in THF and was cooled to −78° C. To this cooled solution was added 6.3 mL of 1.6M n-BuLi in hexanes via syringe over a 5 min period. The reaction mixture was stirred for an additional 5 min then was quenched by adding 50 mL of water dropwise. This mixture was warmed to room temperature then was extracted 2×150 mL ethyl acetate.

Step 5.

To a 50 mL Schlenk tube were added the ligand (2.93 g, 6.03 mmol), Ir(acac)$_3$ (0.59 g, 1.205 mmol) and tridecane (50 drops). The mixture was degassed and heated in a sand bath with stirring under a nitrogen for 73 h. After cooling, the reaction mixture was dissolved with a mixture of solvent (CH$_2$Cl$_2$:hexanes=1:1) and subject to flash column chromatography with 1:1 CH$_2$Cl$_2$:hexanes as the eluent. The solid after column chromatography was recrystallized from a mixture of CH$_2$Cl$_2$ and methanol to yield 1.18 g of product.

Synthesis of Compound 4

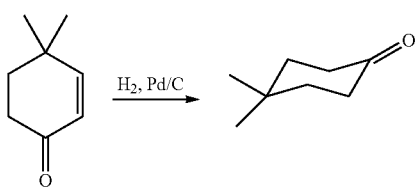

Step 1.

10.0 g (0.08 mol) of 4,4-dimethylcyclohex-2-enone was dissolved in 150 mL of ethanol. This solution was added to a Parr hydrogenation vessel that was purged with nitrogen and was charged with 0.5 g of 10% palladium on activated carbon. This heterogeneous mixture was shaken on the Parr hydrogenator for 8 h. The reaction mixture was filtered through Celite and evaporated to dryness to yield 7.9 g of product.

Step 2.

A mixture of p-tolylsulfonylhydrazine (6.8 g, 36.7 mmol), 60 mL of absolute ethanol and the ketone (4.64 g, 36.76 mmol) was heated to reflux at 100° C. After heating for 2 h, the reaction mixture was cooled using an ice-water bath to precipitate the majority of the hydrazone. The resulting solid was collected by filtration and was washed thoroughly with ice-cold ethanol. Air drying for 1 h afforded 7.67 g of the required hydrazone.

Step 3.

To a dried 500 mL round-bottom flask equipped with a magnetic stirbar and rubber septum, hydrazone (5 g, 17 mmol) was added followed by 100 mL of anhydrous hexanes. To this mixture 100 mL of anhydrous TMEDA were added, and the reaction mixture was cooled to −78° C. and maintained at this temperature for 15 min, after which 60.6 mL (84.9 mmol) of 2.5M sec-BuLi was added over 15 min. The reaction mixture was then stirred for 1 h at −78° C. and then brought to room temperature and stirred for 1.5 h. The mixture was cooled down to −78° C. again and 15.8 g (84.9 mmol) of pinacol isopropyl borate was then added. The reaction was stirred for another hour at −78° C. and then brought to room temperature and stirred for 3 h. The reaction was quenched with the addition of saturated $NH_4Cl$ and then extracted three times with ether. The combined organic extracts were dried over anhydrous $MgSO_4$, filtered, and concentrated in vacuo. The residue was subject to flash chromatography (40% $CH_2Cl_2$ in hexanes) to afford 1.53 g (38%) of desired product.

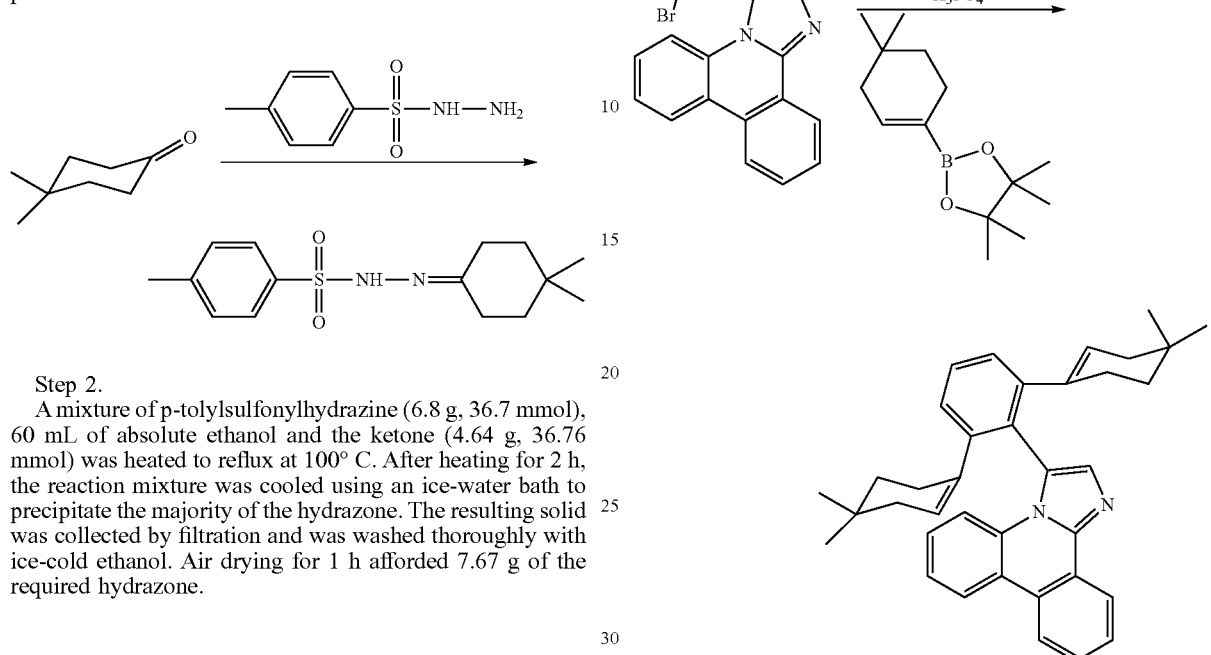

Step 4.

To a 200 mL flask was added dibromide (5 g, 11.06 mmol), bornic acid pinacol ester from step 3 (11.26 g, 47.67 mmol), $Pd(OAc)_2$ (819 mg, 3.64 mmol), dicyclohexylphosphino-2',6'-dimethoxybiphenyl (2.9 g, 7.3 mmol), potassium phosphate tribasic monohydrate (12.73 g, 55.29 mmol), 150 mL of toluene and 150 mL of water. The reaction mixture was fully degassed by freezing-pump-thaw technique. The reaction was heated to reflux and stirred under a nitrogen atmosphere for 16 h. The reaction mixture was filtered through a pad of Celite. The toluene layer was separated from the filtrate. The aqueous layer was extracted 75 mL of toluene. The toluene extracts were combined, dried over sodium sulfate, then were filtered and concentrated under vacuum. The crude product was passed through a silica gel column. The column was eluted with 10% ethyl acetate in hexanes to yield 4.5 g of desired product.

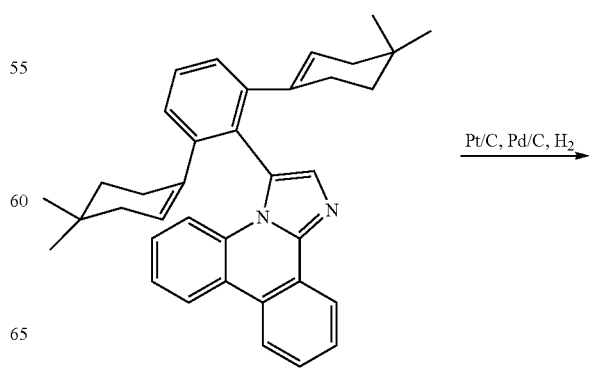

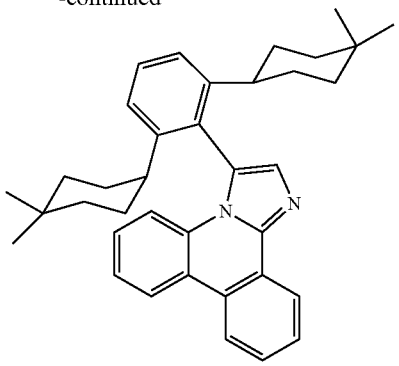

Step 5.

4.5 (8.81 mol) of the cyclohexenyl product from step 4 was dissolved in 150 mL of toluene. This solution was added to a Parr hydrogenation vessel that was purged with nitrogen and was charged with 3.2 g of 10% palladium on activated carbon and 2.8 g of Platinum, 5 wt % (dry basis) on activated carbon wet, Degussa type F101. This heterogeneous mixture was shaken on the Parr hydrogenator for 16 h. The reaction mixture was filtered through a pad of Celite. The toluene filtrate was concentrated under vacuum. The crude product was passed through a silica gel column. The column was eluted with 10% ethyl acetate in hexanes to yield 4.24 g of product.

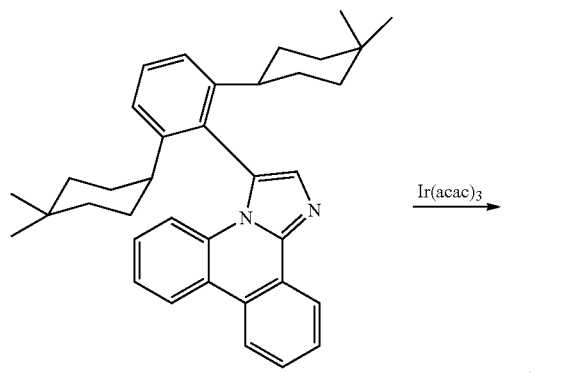

Compound 4

Step 6.

To a 50 mL Schlenk tube were added ligand (2.57 g, 5.03 mmol), Ir(acac)$_3$ (0.495 g, 1.006 mmol) and tridecane (50 drops). The mixture was degassed and heated in a sand bath with stirring under a nitrogen atmosphere for 73 h. After cooling, the reaction mixture was dissolved with a mixture of solvent (CH$_2$Cl$_2$:dexanes=1:1) and subject to flash column chromatography (CH$_2$Cl$_2$:dexanes=1:1). The solid after column chromatography was recrystallized from a mixture of CH$_2$Cl$_2$ and methanol to yield 0.8 g of product.

Synthesis of Compound 5

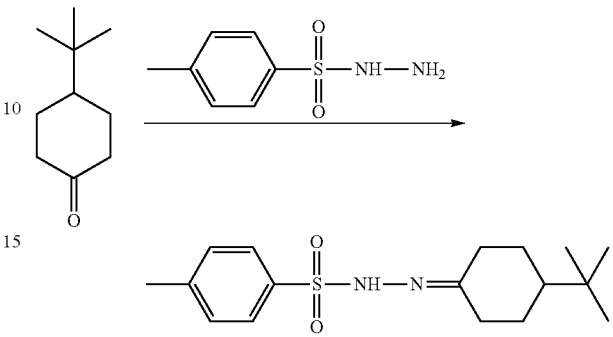

Step 1.

A mixture of 4-tert-butylcyclohexanone (26.5 g, 0.172 mol), p-toluenesulfonylhydrazide (31.74 g, 0.171 mol) and 450 mL of anhydrous ethanol was heated to reflux for 4 h then cooled to room temperature. The reaction mixture was filtered and dried under vacuum to yield 35 g of product.

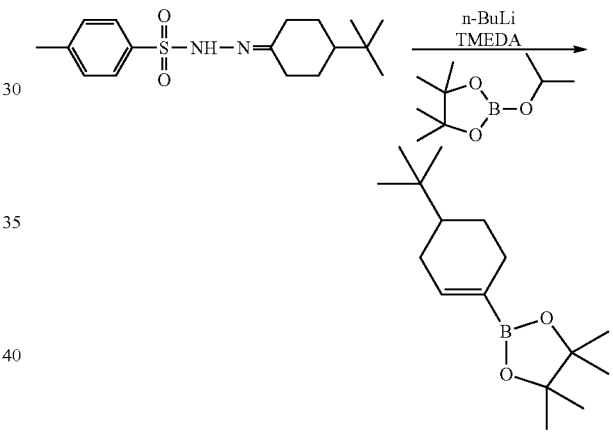

Step 2.

To a dried 500 mL round-bottom flask equipped with a magnetic stirbar and rubber septum, hydrazone (7.5 g, 0.023 mol) was added followed by 70 mL of anhydrous hexanes. To this mixture 70 mL of anhydrous TMEDA was added and the reaction mixture was cooled to −78° C. and maintained at this temperature for 15 min, after which 37 mL (0.092 mol) of 2.5M n-BuLi in hexanes were added over 15 min. The reaction mixture was then stirred for 1 h at −78° C. and then brought to room temperature and stirred for 3.5 h. The mixture was brought to −78° C. again and 17 g (0.092 mol) of pinacol isopropyl borate were added. The reaction was stirred for another hour at −78° C. and then brought to room temperature and stirred for overnight. The reaction was quenched with the addition of saturated NH$_4$Cl and then was partitioned with 200 mL of ether. This heterogeneous mixture was passed through a Celite pad. The ether layer was separated and the aqueous was extracted 300 mL of ether. The combined organic extracts were dried over anhydrous MgSO$_4$, filtered, and concentrated under vacuum. The crude product was passed through a silica gel column (20-40% methylene chloride/hexanes). 4.4 g (72% yield) of product was obtained.

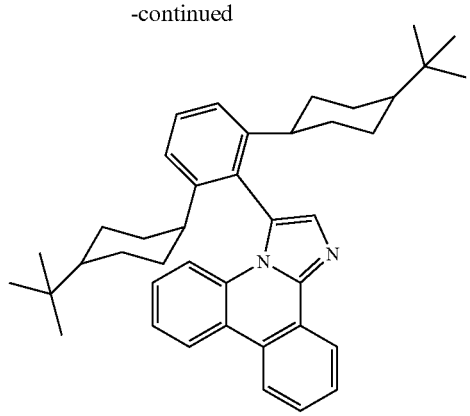

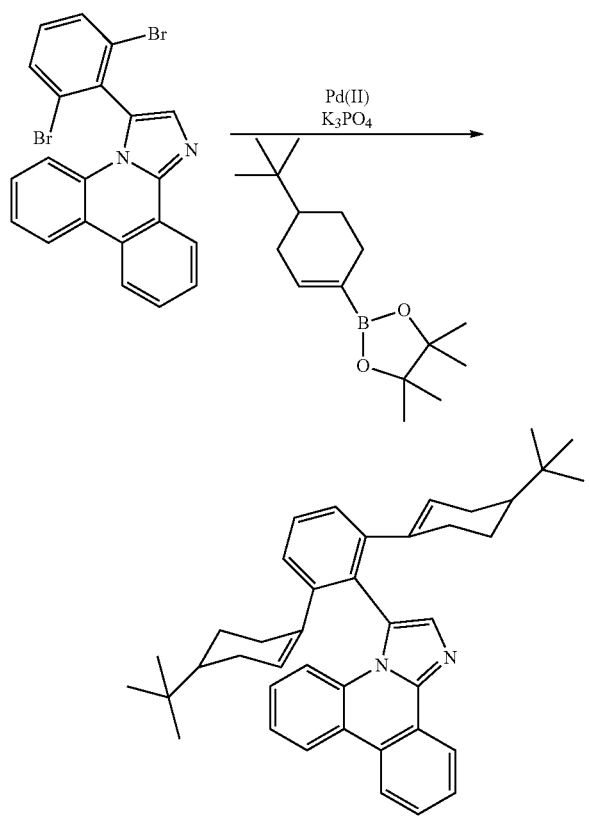

Step 3.

To a 1 L round bottom flask was added dibromide (5 g, 0.011 mol), boronic acid pinacol ester from step 2 (7.3 g, 0.0276 mol), tris(dibenzylideneacetone)dipalladium(O) (0.2 g, 0.22 mmol), dicyclohexylphosphino-2',6'-dimethoxybiphenyl (0.36 g, 0.88 mmol), potassium phosphate tribasic monohydrate (14.0 g, 0.066 mol), 300 mL of toluene and 80 mL of water. The reaction mixture was evacuated and back-filled with nitrogen. The reaction was then heated to reflux and stirred under a nitrogen atmosphere for 16 h. The heterogeneous reaction mixture was filtered through a pad of Celite. The toluene layer was separated and the aqueous was extracted 100 mL of toluene. The toluene portions were combined and dried over magnesium sulfate. This dried organic mixture was then filtered and concentrated under vacuum. The crude product was purified by silica gel chromatography. The column was eluted with 1-4% ethyl acetate/methylene chloride. 5 g (80% yield) of product was obtained.

Step 4.

The alkenyl product (5.0 g, 0.0088 mol) from Step3 was dissolved in 200 mL of toluene and was charged into a Parr hydrogenation bottle that already contained 3.8 g of 10% Pd/C and 3.0 g of 5% Pt/C Degussa Type F101 RA/W. This mixture was placed on the Parr hydrogenator for 58 h. The reaction mixture was filtered through a pad of Celite and the pad was rinsed with 200 mL of toluene. The toluene filtrate was concentrated under vacuum to yield 4.3 g of crude product. The crude product was purified by silica gel chromatography. The column was eluted with 1-5% ethyl acetate/methylene chloride. Next, the product obtained from the column was dissolved in 50 mL of methylene chloride and was stirred at room temperature for 18 h with 1.1 g of Si-TAAcoH and 1.1 g of Si-Thiourea. This is to remove any residual palladium. The product obtained (3.9 g, 0.0068 mol) was dissolved in THF and was cooled to −78° C. To this cooled solution was added 5.8 mL of 1.6 M n-BuLi in hexanes via syringe over a 5 min period. The reaction mixture was stirred for an additional 5 minutes then was quenched by adding 50 mL of water drop wise. This mixture was warmed to room temperature then was extracted 2×150 mL ethyl acetate. These extracts were dried over magnesium sulfate then were filtered and concentrated under vacuum. These extracts were then passed through a neutral alumina (deactivated by the addition of 6% (w/w) water) column that was eluted with 30-60% methylene chloride/hexanes. 3.6 g of product was obtained. The product obtained from the neutral alumina column was recrystallized from hexanes/ethyl acetate. 2.90 g of product was obtained.

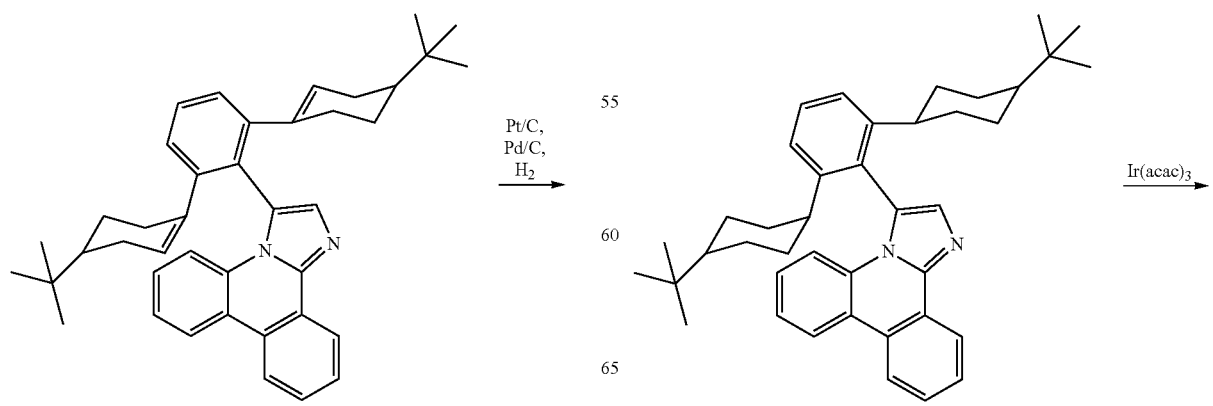

-continued

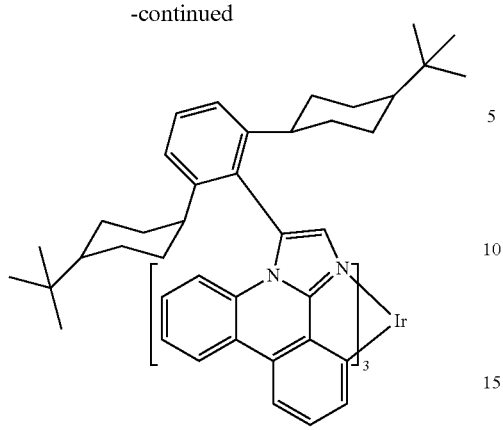

Compound 5

Step 5.

To a 50 mL Schlenk tube were added ligand (2.78 g, 4.86 mmol), Ir(acac)₃ (0.478 g, 0.97 mmol) and tridecane (50 drops). The mixture was degassed and heated in a sand bath with stirring under a nitrogen for 70 h. After cooling, the reaction mixture was dissolved with a mixture of solvent (CH₂Cl₂:dexanes=1:1) and subject to flash column chromatography CH₂Cl₂:hexanes=1:1). The solid after column chromatography was recrystallized from a mixture Of CH₂Cl₂ and methanol to yield 1.0 g of product.

Device Examples

All device examples were fabricated by high vacuum (<10⁻⁷ Torr) thermal evaporation. The anode electrode is 1200 Å of indium tin oxide (ITO). The cathode consisted of IOA of LiF followed by 1000 Å of Al. All devices were encapsulated with a glass lid sealed with an epoxy resin in a nitrogen glove box (<1 ppm of H₂O and O₂) immediately after fabrication, and a moisture getter was incorporated inside the package.

The organic stack of the Device Examples 1 and 2 in Table 2, consisted of sequentially, from the ITO surface, 10 nm of H3 or H4 as the hole injection layer (HIL), 30 nm of 4,4'-bis[N-(1-naphthyl)-N-phenylamino]biphenyl (α-NPD) as the hole transporting later (HTL), 30 nm of the H2 doped with 9% of the dopant emitter (e.g., invention Compounds 1-2) as the emissive layer (EML), 5 nm of H2 as the ETL2 and 40 nm of Alq as ETL1.

Comparative Examples 1-3 were fabricated similarly to the Device Examples except E1, E2, or E3 was used as the emissive dopant and H1 was used as the host in the EML and as the ETL2 material.

As used herein, the following compounds have the following structures:

H1

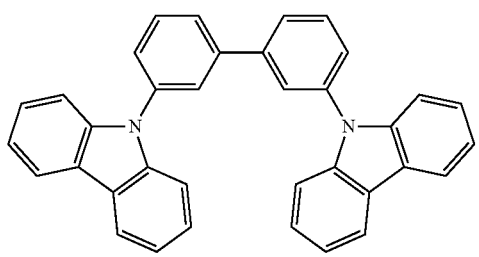

H2

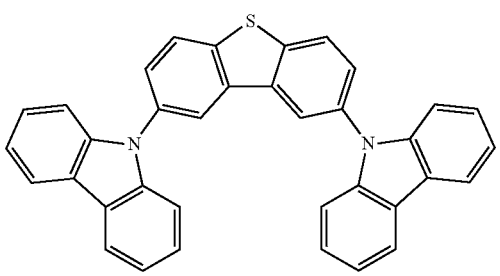

H3

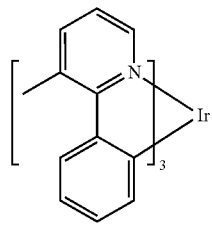

H4

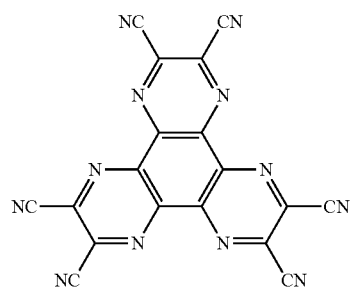

E1

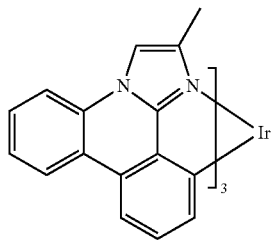

E2

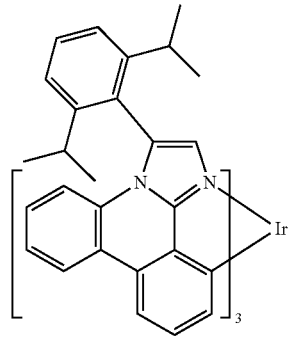

-continued

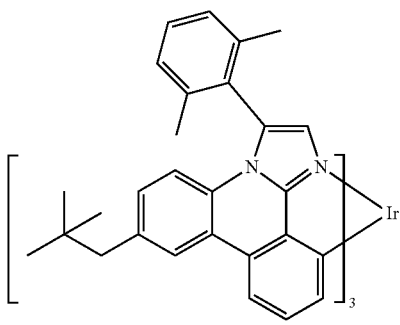

E3

Particular emissive dopants for the emissive layer of an OLED are provided which may lead to devices having particularly good properties. The device structure and the results from device testing are provided in Table 2. Devices having an emissive layer using Compounds 1 and 2 as the emissive dopant show improved device efficiency and stability as well as improved color indicating that these substituted imidazophenanthridine compounds may be beneficial.

Solid state photoluminescent quantum yields (PL %) were determined from 1 weight % of the dopant in polymethylmethacrylate (PMMA), an optically inert polymer matrix. The samples are prepared by dissolving the dopant and PMMA in 1 mL of toluene per 100 mg solids (90 mg of PMMA and 10 mg of the dopant). The samples were filtered and drop-casted onto a pre-cleaned quartz substrate. After the solvent has evaporated, PL quantum yields were measured using a Hamamatsu Absolute PL Quantum Yield Measurement System. The system is comprised of an integrating sphere, xenon light source, monochromater, and multi-channel CCD spectrometer, and is housed in an inert atmosphere glove box to prevent quenching by oxygen. The excitation wavelength was 342 nm.

thermore, Comparative example 3 uses E3 which has a bulky neopentyl group substituted on the other ring of the ligand, yet this does not lead to a large improvement in PL quantum yield. Compounds 1 and 2 with bulky alkyl groups substituted to the twisted aryl are found to have higher PL quantum yield and therefore improved device efficiency. Alkyl groups particularly beneficial as these lead to minimal red-shifting. The use of bulky alkyl substituents (i.e., alkyl groups containing four or more atoms) is believed to be a novel way to modify the compound to inhibit self quenching. These bulky substituted compounds do not suffer the lifetime limitation of compounds having alkyl groups substituted to the 4-imidazole position, as seen for E1 used in Comparative Example 1.

Attaching a methyl group to the 2 position of the imidazophenanthridine, as shown for E1 in Comparative example 1, increased solid state quantum yield of the dopant and lead to higher device efficiency. However, several examples demonstrated that the addition of alkyl substituents at this position can lead to devices having short lifetimes (i.e., less than 100 hours at 2000 nits). Alternatively, it was found that attaching bulky alkyl groups (i.e., alkyls having four or more atoms) increased photoluminescent efficiency and device efficiency. For example, Compounds 1 and 2 have high efficiency, similar to Comparative example 1, and greater efficiency than Comparative examples 2 and 3. Both the selection of bulky alkyl substituents and the site of substitution (i.e., 2 and/or n position of the twisted aryl) may be important to obtain the increased efficiency. For example, E3 used in Comparative example 3 has a bulky neopentyl group substituted away from the imidazole, yet this compound has a relatively low PL yield of 40%. Notably, the compounds provided herein demonstrate significantly long device lifetimes. For example, the device lifetime of invention Compounds 1 and 2 are 3-4 times longer when compared to

TABLE 2

| Device Example | Emitter (doping %) | EQE (%) at 1000 cd/m² | V (V) at 1000 cd/m² | T₁/₂ (h) at 2000 cd/m² | CIE | Sublimation temp. (° C.) | HIL | HOST | ETL2 | PL % |
| --- | --- | --- | --- | --- | --- | --- | --- | --- | --- | --- |
| Comparative 1 | E1 (9) | 12 | 8 | 70 | 0.15, 0.23 | 330 | H3 | H1 | H1 | 52 |
| Comparative 2 | E2 (9) | 7 | 8 | 200 | 0.15, 0.24 | 300 | H4 | H1 | H1 | 26 |
| Comparative 3 | E3 (9) | 8 | 8 | 180 | 0.15, 0.26 | 320 | H4 | H1 | H1 | 40 |
| 1 | 1 (9) | 12 | 7 | 200 | 0.15, 0.24 | 265 | H3 | H2 | H2 | 56 |
| 2 | 2 (9) | 12 | 8 | 300 | 0.15, 0.23 | 310 | H4 | H2 | H2 | 60 |

From Device Examples 1 and 2, it can be seen that the device efficiencies correlate with the solid state PL quantum yields. Comparative Example 1 gives a higher PL efficiency compared to Comparative Example 2. It is believed that the alkyl substitution present in E1 used in Comparative Example 1 inhibits self quenching leading to higher PL and EL efficiencies. Comparative Example 2 uses E2 which has 2,6-dimethyl twisted aryl groups and relatively low PL quantum efficiencies. In these cases the 2,6 alkyl substitutions are not bulky enough to inhibit self quenching. Furthermore, Comparative example 1. Bulky alkyl substitution on the twisted aryl may also improve device processing. For example, Compound 1 has an isobutyl substitution and has a sublimation temperature of 265° C., which is the lowest sublimation temperature to be observed to date in this family of imidazo[1,2-f] phenanthridine iridium complexes.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound having the formula:

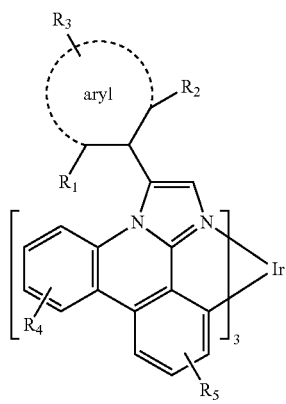

wherein $R_1$ and $R_2$ are independently selected from the group consisting of hydrogen, alkyl, and aryl;

wherein at least one of $R_1$ and $R_2$ is an alkyl that is (i) cyclic, (ii) has four or more carbon atoms, and (iii)(a) is a branched alkyl, (b) is a bicyclic alkyl, or (c) is a multicyclic alkyl;

wherein $R_3$ and $R_4$ may represent up to tetra-substitutions;

wherein $R_5$ may represent up to tri-substitutions; and wherein $R_3$, $R_4$, and $R_5$ are independently selected from the group consisting of hydrogen, alkyl, and aryl.

2. The compound of claim 1, wherein the alkyl that is cyclic and has four or more carbon atoms is a branched alkyl.

3. The compound of claim 1, wherein the alkyl that is cyclic and has four or more carbon atoms is a bicyclic alkyl.

4. The compound of claim 1, wherein the alkyl that is cyclic and has four or more carbon atoms is a multicyclic alkyl.

5. The compound of claim 1, wherein the alkyl that is cyclic and has four or more carbon atoms does not include any heteroatoms.

6. The compound of claim 1, wherein the alkyl that is cyclic and has four or more carbon atoms is a heteroalkyl that contains at least one of an oxygen atom, a nitrogen atom, or a sulfur atom.

7. The compound of claim 1, wherein $R_1$ and $R_2$ are the same.

8. The compound of claim 1, wherein $R_1$ and $R_2$ are different.

9. The compound of claim 1, wherein one of $R_1$ and $R_2$ is an aryl.

10. The compound of claim 1, wherein the compound has the formula:

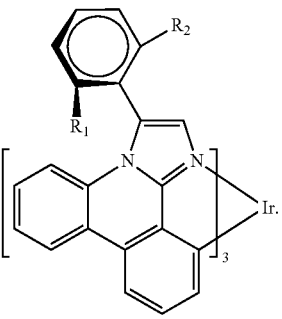

11. The compound of claim 1, wherein the compound is selected from the group consisting of:

Compound 4

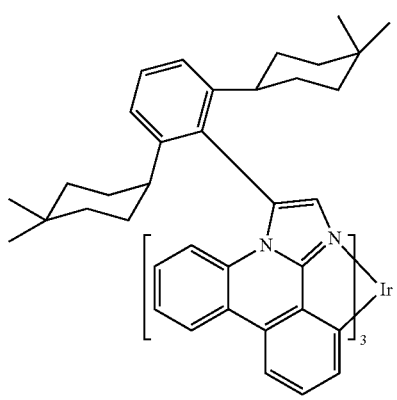

Compound 5

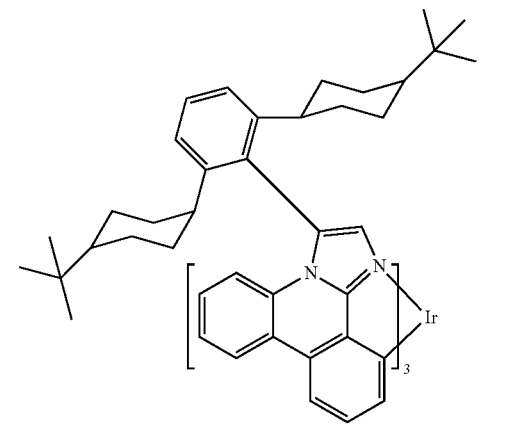

Compound 7

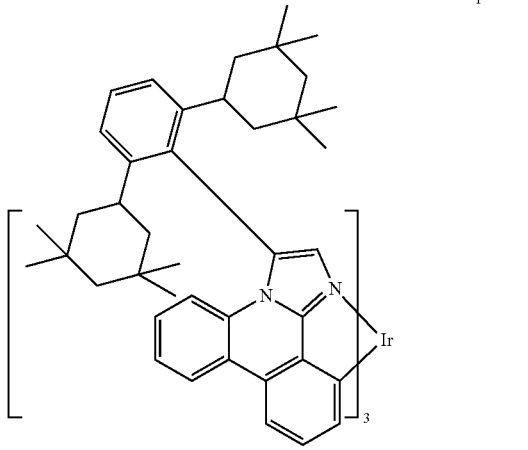

Compound 8
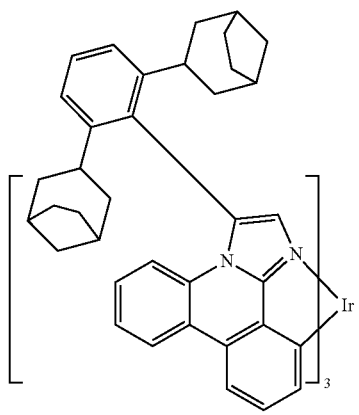
Compound 15
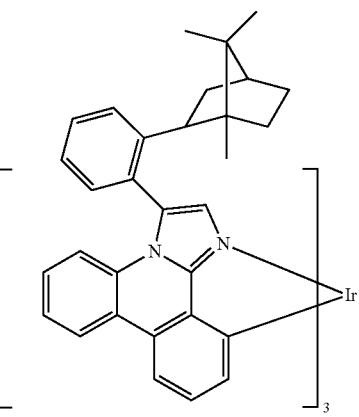
Compound 10
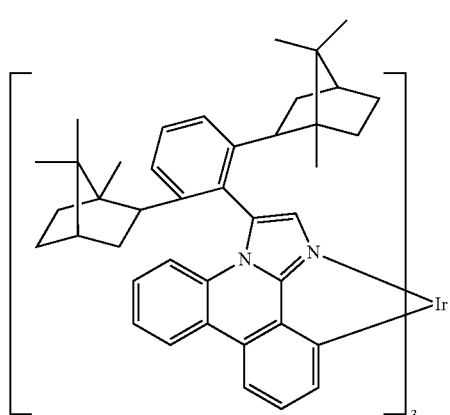
Compound 16
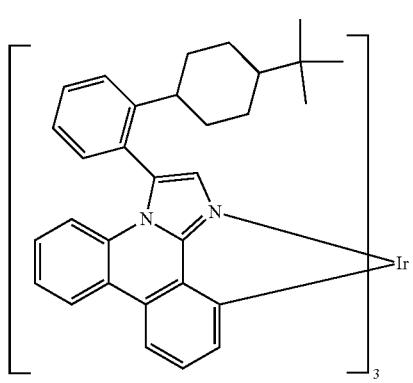
Compound 12
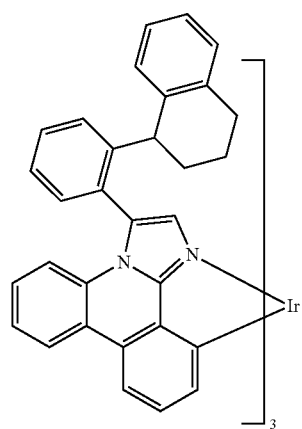
Compound 19
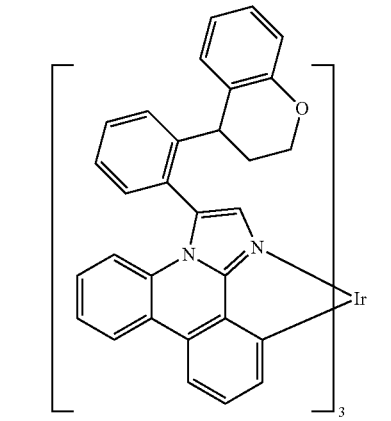
Compound 14
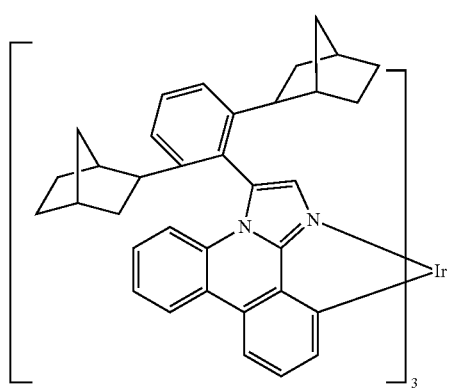
Compound 20
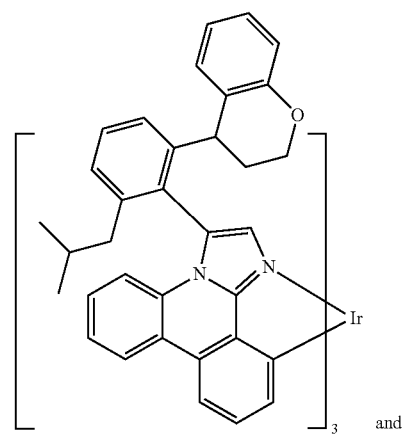
and Compound 31

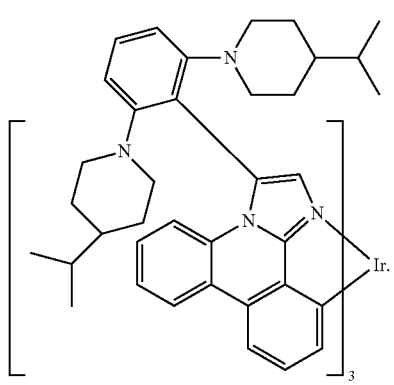

Compound 4

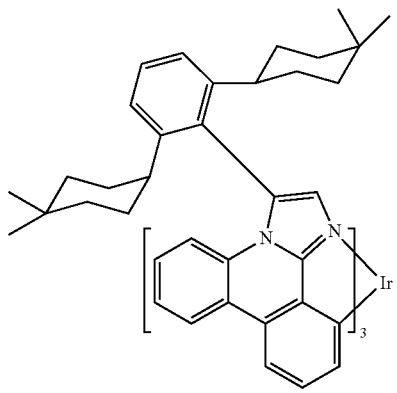

12. A first device comprising an organic light emitting device, further comprising:

an anode;

a cathode; and an organic layer, disposed between the anode and the cathode, the organic layer comprising a compound having the formula:

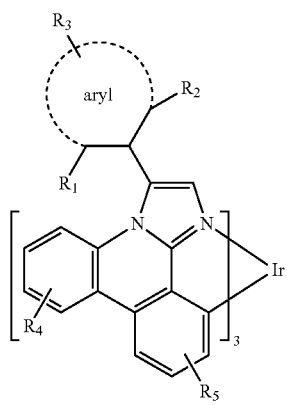

Compound 5

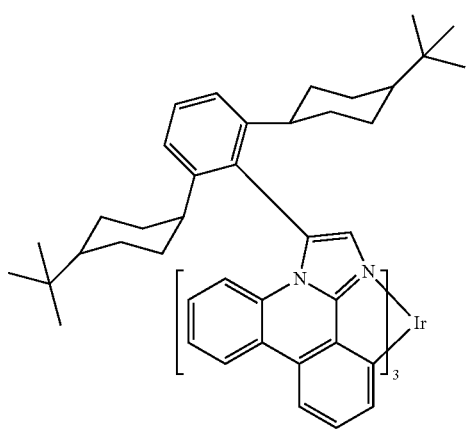

wherein $R_1$ and $R_2$ are independently selected from the group consisting of hydrogen, alkyl, and aryl;

wherein at least one of $R_1$ and $R_2$ is an alkyl that is (i) cyclic, (ii) has four or more carbon atoms, and (iii)(a) is a branched alkyl, (b) is a bicyclic alkyl, or (c) is a multicyclic alkyl;

wherein $R_3$ and $R_4$ may represent up to tetra-substitutions;

wherein $R_5$ may represent up to tri-substitutions; and wherein $R_3$, $R_4$, and $R_5$ are independently selected from the group consisting of hydrogen, alkyl, and aryl.

13. The first device of claim 12, wherein the first device is a consumer product.

14. The first device of claim 12, wherein the compound is selected from the group consisting of:

Compound 7

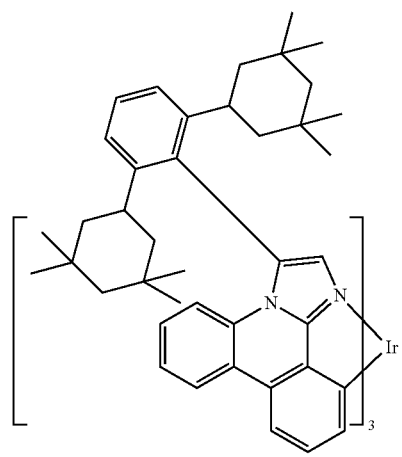

Compound 8
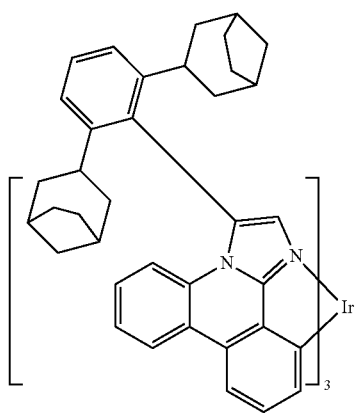
Compound 10
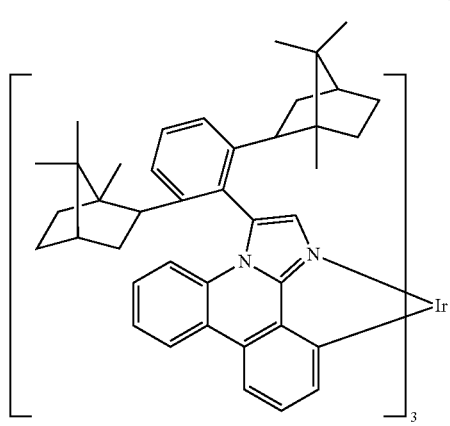
Compound 12
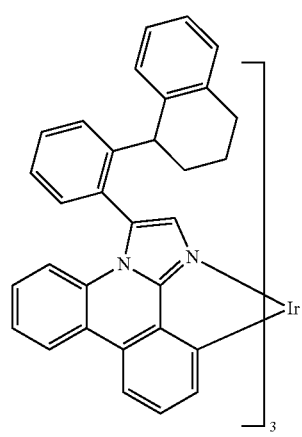
Compound 14
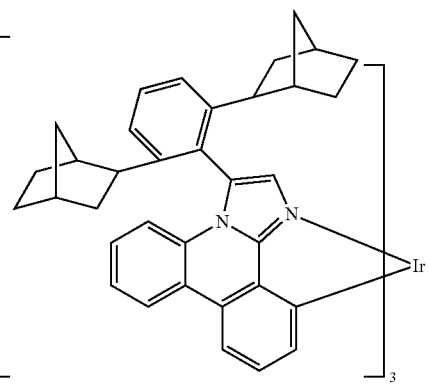
Compound 15
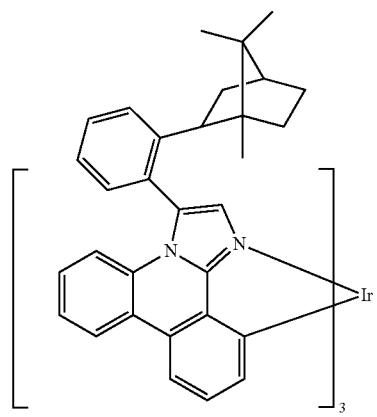
Compound 16
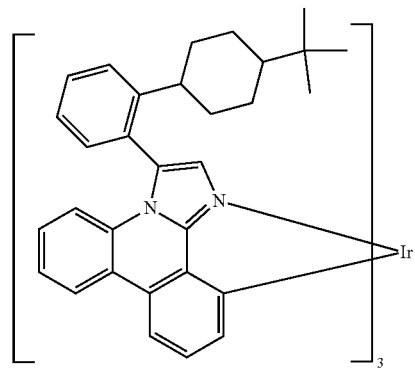
Compound 19
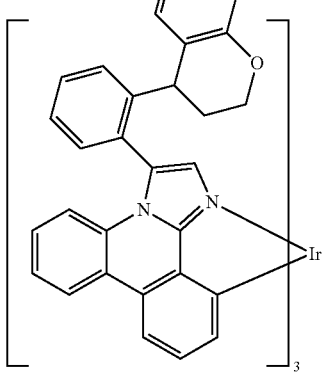

Compound 20

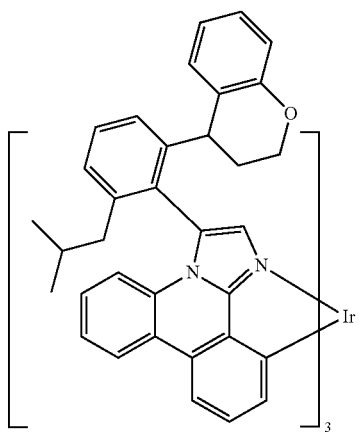

Compound 31

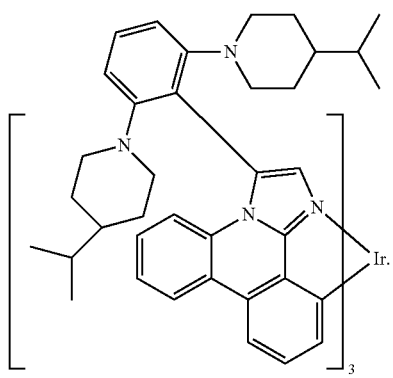

15. The first device of claim 12, wherein the organic layer further comprises a second compound selected from the group consisting of:

Compound 1

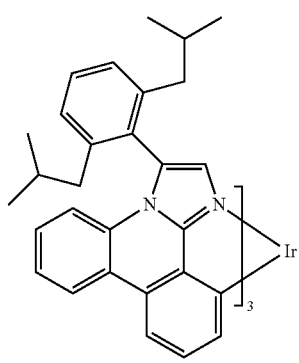

Compound 2

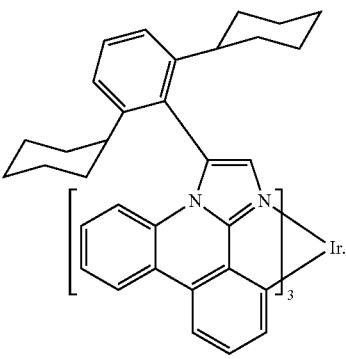

16. The first device of claim 12, wherein the organic layer is an emissive layer and the compound having the formula

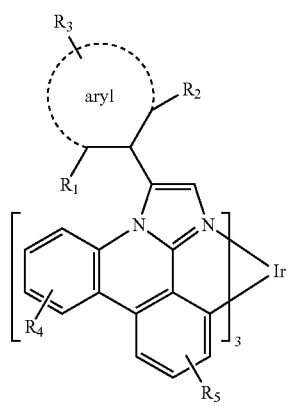

is an emissive compound.

17. The first device of claim 12, wherein the organic layer further comprises a host having the formula:

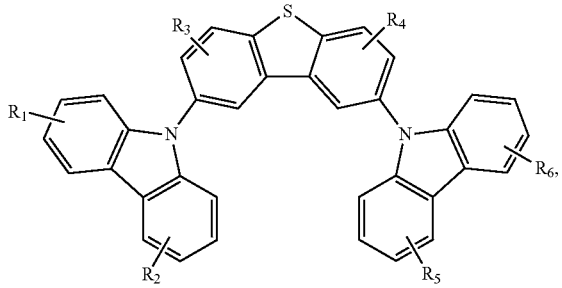

wherein each of $R_1$ through $R_6$ are independently selected from the group consisting of any alkyl, alkoxy, amino, alkenyl, alkynyl, arylalkyl, aryl, heteroaryl and hydrogen, and where each of $R_1$ through $R_6$ may represent multiple substitutions.

* * * * *